United States Patent [19]

Grimshaw et al.

[11] Patent Number: 5,085,749
[45] Date of Patent: Feb. 4, 1992

[54] DYNAMICALLY CONTROLLED MEMBRANE

[75] Inventors: Paul E. Grimshaw, Arlington; Alan J. Grodzinsky, Lexington; Martin L. Yarmush, Sharon, all of Mass.

[73] Assignee: Massachusetts Institute of Technology, Cambridge, Mass.

[21] Appl. No.: 384,722

[22] Filed: Jul. 24, 1989

Related U.S. Application Data

[63] Continuation-in-part of Ser. No. 324,381, Mar. 14, 1989.

[51] Int. Cl.$^5$ .......................... C25B 1/00; B01D 61/42
[52] U.S. Cl. ........................ 204/182.1; 204/182.3; 204/182.6; 204/180.1; 204/301
[58] Field of Search .............. 204/180.1, 182.6, 182.1, 204/182.3, 301

[56] References Cited

U.S. PATENT DOCUMENTS 4,161,013  7/1979  Grodzinsky et al. ............... 361/433

OTHER PUBLICATIONS

Weiss, A. M. et al., AIChE Symposium Series, Chemically and Electrically controlled membranes (1986).
Kost, J. et al., J. Biomed. Materials Res., 19: 1117-1133 (1985).
Protein Transport Across Electrically Controlled Membranes, Grimshaw et al. (Grimshaw 2).
Dynamic Membranes for protein transport: Chem. & Elec. control Grimshaw et al. (1989).
Grimshaw, P. E. et al., Chem. Eng. Sci, 44(4) 827-840 (1989).
Firestone, B. A. and Siegal, R. A., Polymer Communications, 29: 204-208 (1988).
Grimshaw, P. E., et al., Abstract 155F, AIChE Annual Meeting (1987).
Nussbaum, J. H. and Grodzinsky, A. J., Abstract 172D AIChE Annual Meeting (1987).
Weiss, A. M., et al., AIChE Symposium Series, 82: 88-98 (1986).
Gehrke, S. H., et al., Chem. Eng. Sci., 41(8): 2153-2160 (1986).
Kost, J., et al., J. Biomed. Materials Res., 19: 1117-1133 (1985).
Eisenberg, S. R. and Grodzinsky, A. J., J. Membrane Sci., 19: 173-194 (1984).

Primary Examiner—John Niebling
Assistant Examiner—Arun S. Phasge
Attorney, Agent, or Firm—Hamilton, Brook, Smith & Reynolds

[57] ABSTRACT

This invention pertains to a method of dynamically controlling the transport of a molecule across a polyelectrolyte membrane whereby chemical modulation of the electrostatic swelling forces in the polyelectrolyte membrane results in large changes in permeability and selectivity and a transmembrane electric field having electroosmotic, electrophoretic and electrostatic effects combine to allow the selective transport of the molecule across the membrane.

10 Claims, 9 Drawing Sheets

DYNAMICALLY CONTROLLED MEMBRANE

RELATED APPLICATION

This application is a continuation-in-part of U.S. Ser. No. 07/324,381, filed Mar. 14, 1989.

BACKGROUND OF THE INVENTION

The ionizable fixed charge groups of polyelectrolyte membranes give rise to important electromechanical and swelling phenomena. These membranes can undergo dramatic changes in bulk dimensions and microstructure by reversibly altering the electrostatic swelling forces arising from polyelectrolyte fixed charge groups, thereby changing transport properties. Further, the presence of membrane fixed charge groups give rise to electrokinetic transport phenomena and electrostatic partitioning of charged solutes.

pH control of the ionization state of crosslinked polymethacrylic acid (PMAA) and polyacrylic acid gels can produce reversible swelling changes. pH-induced anisotropic length changes in oriented polyacrylic acid filaments can be used to raise and lower mechanical loads. The extent of swelling is limited by the degree of membrane crosslinking.

The process of gel extraction uses pH-sensitive gels to separate and concentrate solutes by selective partitioning of the solutes within the gels, rather than selective permeability. In this process, as the gel ionizes, it swells, imbibing water and only those solutes accessible within the gel. The gel is removed and the remaining solution contains an elevated concentration of those solutes excluded from the gel. The partitioning of solutes in these gels is selective on the basis of solute, size, and charge (for example, by Donnan partitioning effects). The extent to which changes in gel swelling affect solute permeability and separation is dependent on membrane composition and crosslink density.

One means by which an applied electric field can alter membrane permeability is direct modification of membrane microstructure. Application of a transmembrane electric field induces phase changes in liquid crystal membranes. Using deformable polyelectrolyte membranes, electric field control of intramembrane pH or ionic strength can regulate changes in membrane hydration, and concomittant changes in membrane permeability. Electrodiffusion mediated changes are known to occur in the bulk hydration of PMAA membranes.

The effect of an electric field on the solute reduces concentration polarization and improves membrane filtration. An applied electric field increases filtration flux by electrophoresis of a retained solute away from a membrane filter, and by electroosmosis of the solvent through the filter and adjacent film. Similar permeability changes can be induced without electric fields by direct manipulation of bath pH and ionic strength to modulate membrane swelling forces.

An additional mechanism for electrical control of solute flux are electrode reactions which induce changes in bath pH. Weiss and co-workers measured 16-fold changes in the permeability of PMAA members to Lis-Maltoheptaose after passing current through bare metal electrodes to electrochemically alter the bath PH. Weiss, A. M., et al., *AIChE Symp. Ser.*, 82:88-98 (1986).

Eisenberg and Grodzinsky demonstrated in collagen membranes exposed to a gradient in either pH or ionic strength, changes of up to 25% in permeability to sucrose by applying a transmembrane electric field. Eisenberg, S. R. and Grodzinsky, A. J., *J. Membrane Sci.*, 19:173-194 (1984).

The biotechnology industry provides an increasing demand for new methods to purify proteins from other cell products and impurites. Suitable techniques must be selective, capable of functioning on a large scale, and must avoid denaturation of proteins. Currently, chromatographic techniques are widely used for protein purification but these are both time consuming and labor intensive. Electrophoresis is well suited to small scale analytical separation, but is generally not practical for large scale purification. Ultrafiltration is a cost effective method used for protein concentration, but it lacks the selectivity needed for purification and has the additional problem of concentration polarization, in which solutes retained at the membrane surface form a compact layer that impedes solvent flux.

SUMMARY OF THE INVENTION

This invention pertains to a method for dynamically controlling the selective transport of a molecule across a polyelectrolyte membrane. The method comprises determining an appropriate pH and an appropriate ionic strength of a bathing solution and an appropriate electric field to be applied across the membrane. The method further comprises contacting the membrane with the bathing solution having the pre-selected pH and pre-selected ionic strength, thereby producing a desired permeability of the polyelectrolyte membrane and applying the pre-selected electric field across the membrane. The membrane is contacted with the bathing solution having a pre-selected pH and a pre-selected ionic strength, and the pre-selected electric field is applied across the membrane such that the combination of electromechanical deformation of the membrane and one or more effects selected from the group consisting of electroosmotic, electrophoretic and electrostatic partitioning allow the desired selective transport of the molecule across the polyelectrolyte membrane. Depending on the molecule to be transported across the membrane, all four of the effects listed above may be dynamically controlled to selectively transport the molecule.

The method of the present invention can be used for protein or amino acid separation wherein a protein or amino acid can be selectively separated from a mixture of proteins or amino acids. In addition, this invention encompasses a selectively controlled drug delivery system wherein the transport of a drug across a polyelectrolyte membrane is dynamically controlled.

The drug delivery system of the present invention comprises a reservoir containing the drug. a bathing solution having a selected pH and a selected ionic strength, and a polyelectrolyte membrane. The drug delivery system further comprises a means for applying a selected current across the membrane, thereby producing an electric field. Further, the pH of the bathing solution, the ionic strength of the bathing solution, and the electric field are selected such that the combination of electromechanical deformation of the membrane and one or more effects selected from the group consisting of electroosmotic, electrophoretic and electrostatic partitioning allow the desired selective transport of the drug across the polyelectrolyte membrane.

The development of a selective, dynamically controlled membrane separation technique greatly improves the separation and purification of proteins. Separation through dynamically controlled membranes can potentially achieve high selectivity by controlling the effective mesh size in a continuous fashion over a range, resulting in a serial separation based on increasing solute size. Through the use of the present method, a single protein or amino acid can be selectively separated from a mixture of proteins or amino acids. In addition, charged solutes can be separated on the basis of both size and charge, adding an element of electrophoresis to further enhance selectivity.

DETAILED DESCRIPTION OF THE INVENTION

Figure 1:
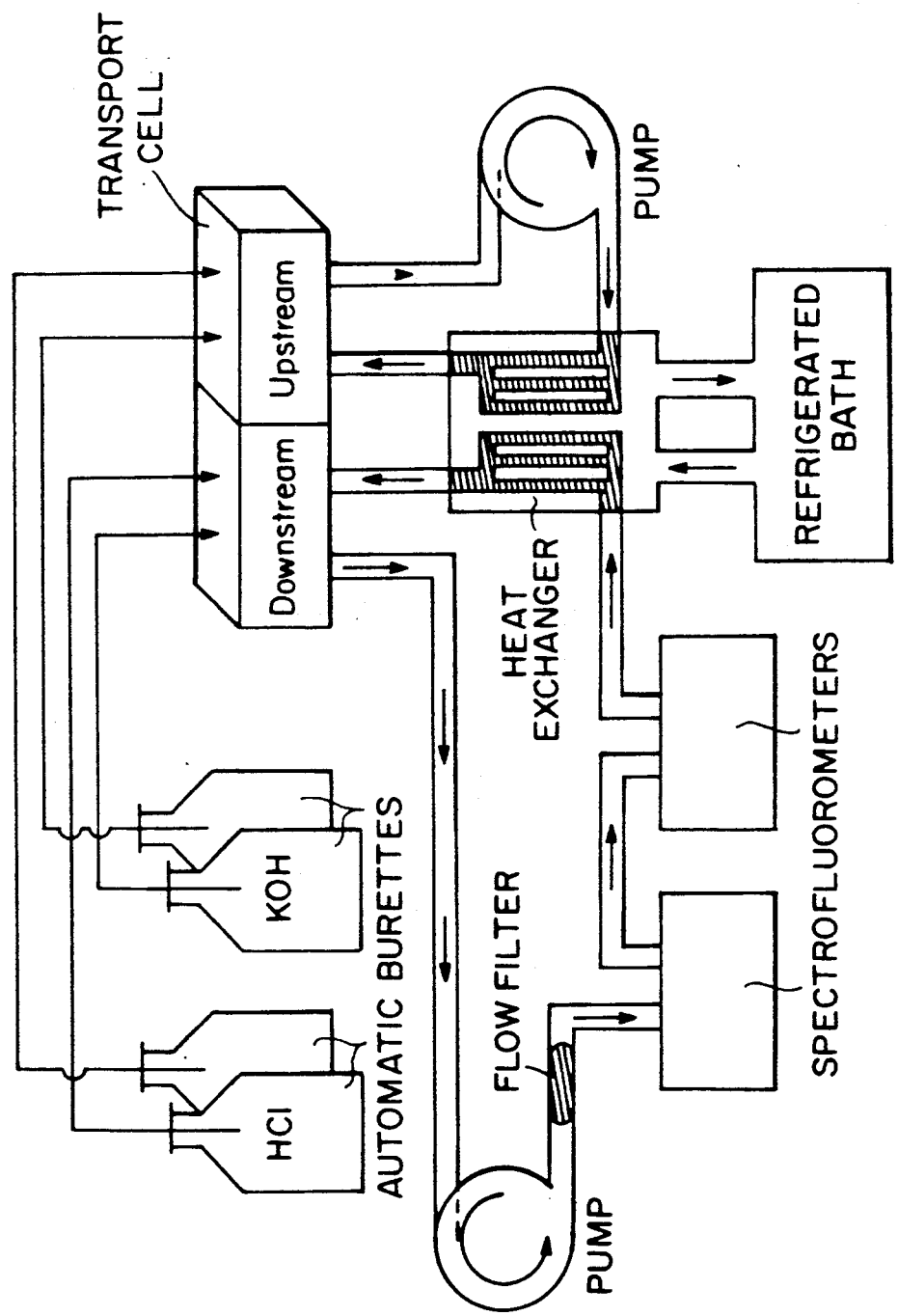
FIG. 1 is a schematic representation of a transport apparatus according to this invention.

This invention pertains to the application of a combination of four distinct mechanisms for chemical and electrical control of protein transport across polyelectrolyte membranes. These mechanisms are (1) electromechanical deformation of the membrane; (2) electroosmotic augmentation of solute flux through the membrane; (3) electrophoretic transport within the membrane; and (4) electrostatic (Donnan) partitioning to alter the diffusive flux across the membrane. Depending on the molecule to be transported across the membrane, all of these mechanisms can be dynamically controlled to selectively transport the molecule. Alternatively, a combination of electromechanical deformation of the membrane and one or more of the effects listed above can selectively transport a molecule, such as a single protein or a single amino acid from a group of proteins or amino acids, across a polyelectrolyte membrane. These mechanisms have been identified, quantified, and delineated from each other. Further, the kinetics of the changes in solute flux associated with each mechanism have been quantified.

Electrophoresis is defined as the movement of small ions and charged molecules in solution under the influence of an electric field. The rate of migration depends on the size and shape of the molecule, the charge carried, the applied current and the resistance of the medium. Electroosmosis is defined as the movement of a liquid out of or through a membrane comprised of a natural or synthetic polymer, under the influence of an electric field. Electrostatic partitioning is defined as the partitioning of charged macrosolutes within a charged membrane under the influence of an electric field. The Donnan equilibrium partition conditions relate the boundary concentrations for each species just inside the membrane to the external bath conditions. Electromechanical deformation of the membrane is defined as changes in the microstructure of the membrane which result from membrane hydration and the application of an electric field.

A molecule capable of being selectively transported across a membrane can be a macromolecule such as a lipid, protein, amino acid, or nucleic acid, an organic salt (e.g., N-(3-sulfopropyl)acridinium inner salt), an inorganic salt, a polysaccharide, or sugar (e.g., dextran). Examples of proteins which can be selectively transported are albumin insulin, interferon, ribonuclease A, and interleukin-2. The molecule to be selectively transported across the membrane can be conjugated to a molecule which can be traced through the membrane. Examples of such tracing molecules include fluorophores, dyes or radioisotopes.

Membranes useful in this invention can be selected from various polyelectrolyte membranes having ionizable fixed charge groups. The membranes can be in a form which allows selective transport of molecules, (e.g., gels, composites, or hollow fibers). Examples of membranes which are useful in the present invention are sulfonic acid polyelectrolytes, such as polystyrene sulfonic acid (PSSA), the sodium salt of polystyrene sulfonic acid (PSSNa), sulfonate polymethyl styrene, and copolymers thereof with other vinyl monomers, and polyvinyl sulfonic acid. Other polyelectrolytes that may be employed include sulfonated polyvinyl naphthalenes, sulfonated polyvinyl anthracenes, sulfonated linear phenol formaldyhyde resins, condensation polyamides and polyesters containing comonomers such as sulfoisosphthalic acid salts.

The membranes of this invention can be hydrophobic (e.g., polyvinylidene fluoride (PVDF), n-alkyl methacrylate ester) or hydrophilic (e.g., cellulose, cellulose acetate, cellulose nitrate or mixtures thereof, acrylic acid, methacrylic acid). Furthermore, it is possible to coat PVDF membranes with materials which render them hydrophilic (e.g., Durapore ®, Millipore Corporation, Bedford, Mass.). Copolymerizing hydrophobic n-aklyl methacrylate ester with N,N-dimethylaminoethyl methacrylate produces a hydrophilic membrane as the amine groups are ionized. Preferred polyelectrolyte membranes are polymethacrylic acid (PMAA) membranes.

Polyelectrolyte membranes which can be used in the method of this invention can be crosslinked to a specific crosslink density to affect membrane pore size. Chemical crosslinking agents useful in this invention can be selected from the various epoxides, amines or aldehydes, for example, epichlorohydrin, boron trifluoridemonoethanolamine complex, epoxidenovolac, polyvinylmethylethermaleic anhydride, the expoxide of bisphenol A, butadiene diepoxide, polystyrene maleic anhydride, formaldehyde, phenol formaldehyde prepolymers, and the like. Preferred crosslinking agents include ethylene glycol dimethacrylate or triethylene glycol dimethacrylate.

In the method of the present invention, a polyelectrolyte membrane is placed in a bathing solution having an appropriate pH or pH gradient, and an appropriate ionic strength, and an appropriate electric field is applied across the membrane. The bathing solution can be selected from various buffer solutions capable of maintaining a selected pH or pH gradient and a selected ionic strength. Examples of buffer solutions which can be used in this invention are potassium phosphate malonic acid, acetic acid, tris (hydroxymethyl) aminomethane (Tris), phosphate buffered saline (NaCl, KCl, Na$_2$HPO$_4$ 7H$_2$O, KH$_2$PO$_4$), 20×SSC (NaCl, Na$_3$ citrate 2H$_2$O, HCl), STE (Tris Cl, NaCl, EDTA), TAE (Tris base, glacial acetic acid, Na$_2$ EDTA), TBE (Tris base, boric acid, EDTA), TE (Tris Cl, EDTA), and 10×TM (Tris Cl, MgCl$_2$) Ausebel et al., *Current Protocols in Molecular Biology*, pp. A2.1-A2.3 (1988).

An appropriate pH which can be used in the present invention is a pH capable of selectively altering the membrane characteristics (i.e., fixed charge groups) to produce a desired permeability of the membrane to a particular molecule. The desired permeability of the membrane is defined as the pore size necessary to selectively allow passage of the molecule through the membrane. A pore size which is particular to a molecule is a pore size which allows selective transport of a molecule across a membrane. An appropriate ionic strength is defined as the ionic strength capable of selectively altering the membrane characteristics to produce a desired permeability of the membrane to a particular molecule. The ionic strength is determined by adding appropriate ions (e.g., Na$^+$, Cl$^-$) to a bathing solution. For example, a physiological buffer (i.e., an ionic strength corresponding to physiological conditions) may be desired when separating proteins which would otherwise denature. An appropriate electric field is defined as that produced by applying a current necessary to produce the electroosmotic, electrophoretic, electrostatic partitioning, and electromechanical deformation effects which allow the selective transport of the molecule across the membrane. The application of an electric field can affect the pH of the membrane by affecting the ionizable charge groups. These values can be determined for a particular molecule by simultaneously solving the Equations set forth in Appendix A.

The method of the present invention can be used to selectively separate a protein or amino acid from a mixture of proteins or amino acids. In a protein separation, the above described phenomena (i.e., electrophoresis, electroosmosis, electrostatic partitioning, electromechanical deformation) interact simultaneously in a separation process to produce the desired selective transport effects. Depending on the molecule to be transported, a combination of electromechanical deformation and one or more effects can be controlled to selectively transport the molecule. In order to selectively transport a particular molecule across a polyelectrolyte membrane, the techniques described in detail in the following examples are applied to a particular molecule and membrane system. The differential equations representative of the electroosmotic, electrostatic partitioning, electrophoretic and electromechanical deformation effects (See Appendix A) can be solved simultaneously using manual or computer techniques.

The method of the present invention also encompasses a real time drug delivery system. A real-time drug delivery system is a system capable of providing on-demand delivery of a drug. A selective, dynamically controlled drug delivery system dynamically controls the transport of a drug across a polyelectrolyte membrane. The phenomena described above can be incorporated into a dynamically controlled, implantable or transdermal drug delivery system for on-demand delivery. A drug is broadly defined herein as any chemical agent that affects living processes (e.g., insulin, interferon, interleukin-2).

The drug can be administered by subcutaneous or other injection, intravenously, parenterally or transdermally via a drug delivery system having a reservoir containing the drug. The form in which the drug will be contained in the reservoir (e.g., solution or emulsion) will depend on the route by which it is administered. The quantity of the drug to be administered will be determined on an individual basis, and will be based at least in part on consideration of the individual's size, the severity of the symptoms to be treated and the result sought.

The invention is further illustrated by the following specific examples, which are not intended to be limiting in any way.

EXAMPLE I: Membrane Formulation

Both neutral and ionizable polyelectrolyte membranes have been used to highlight the importance of membrane charge groups. PMAA membranes acquire a negative fixed charge density through the dissociation of carboxylic acid groups. Crosslinked PMAA membranes are made by copolymerizing methacrylic acid (Polysciences, Inc., Warrington, Pa.) with a crosslinker in the presence of initiators, as previously described. Weiss, A. M., et al., AIChE Symposium Ser., 82:88-98 (1986). One series of membranes was crosslinked with ethylene glycol dimethacrylate (Polysciences, Inc.) at a concentration of 4% of the total monomer, and is designated the S.4/1 formulation. Another series, the S.05/1 formulation, was crosslinked with triethylene glycol dimethacrylate (Polysciences, Inc.) at a concentration of 0.5% of the total monomer. The monomer concentration was 67% (v/v) in solution for both formulations.

Neutral membranes of crosslinked polyacrylic acid (PA) are made using electrophoresis grade acrylamide and N, N'-methylene-bis-acrylamide crosslinker (Bio-Rad Laboratories, Richmond, Calif.), filtered through a mixed bed ion exchange resin to remove trace amounts of charged monomer. A crosslinker content of 2.7% of the total monomer and a total monomer concentration of 10% (w/v) in solution were used, since this formulation gave PA membranes whose water content was similar to that of the S.05/1 membranes at neutral pH. Both the PMAA and PA membranes were cast between two glass plates separated by a polytetrafluoroethylene (PTFE) spacer ranging from 75 to 1000 μm to obtain membranes of various thickness.

EXAMPLE II: Equilibrium Membrane Hydration vs pH

The equilibrium membrane hydration of polyelectrolyte membranes was measured in bathing solutions of selected pH. Cylindrical disks 2 cm in diameter were cut from PMAA (S.05/1) and PA membranes and equilibrated for at least 24 hours in solutions of 90 mM KCl solutions plus 10 mM buffer (either malonic acid (pH 5.5-6.5), acetic acid (pH 4-5), potassium phosphate (pH 6.5-7.5), or Tris (pH 7.5-8.5)). The disks were then removed from the solution, blotted with a tissue to remove all surface fluid, and weighed in a covered dish to prevent evaporative water loss. The samples were subsequently washed in deionized water for several days to remove salts, dried in vacuo, and weighed. The hydration (H), defined as the ratio of fluid volume to dry polymer volume, was calculated from wet and dry weights using a density of 1.00 for the buffer solutions, 1.33 for PMAA and 1.22 for PA. Hasa, J. and Ilavsky, M., J. Polym. Sci. Polym. Phys. Ed., 13:263-274 (1975). (PA density was assessed from the displacement of water after immersion of membrane specimens). PMAA membrane hydration measurements were repeated using buffered 40 mM KCL solutions.

In these tests, a separate disk from each membrane type was equilibrated at each pH. Each data point (FIG. 2) corresponds to the mean of three wet weights of that disk and the standard deviation for each set of three weights was at most 7% of the mean. A separate set of experiments was performed to evaluate the dependence of the hydration and permeability properties of membranes on membrane formulation (i.e., water content and crosslink density). Adler, K. A., Master's Thesis, MIT, EECS, (1988). The variation in hydration was less than 5% between disks cut from a single membrane and between disks cut from separately cast membranes of identical formulation.

Figure 2:
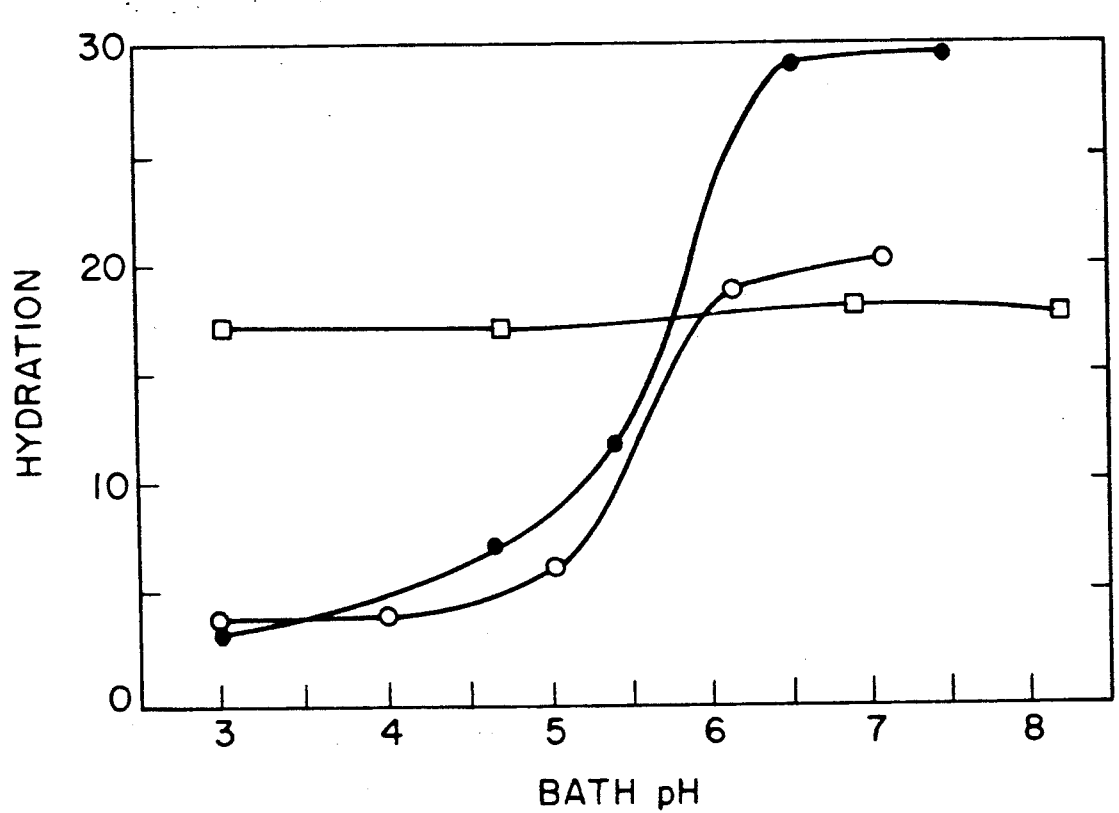
FIG. 2 is a graphic representation of the equilibrium membrane hydration of S.05/1 PMAA (o) and PA membrane (□) at ~100 mM ionic strength (90 mM KCl plus 10 mM pH buffer); and PMAA membranes (●) equilibrated in 40 mM KCl plus 10 mM pH buffer.

The hydration of PMAA membranes increased dramatically with increasing pH, as seen in FIG. 2. This increase is attributed to increased electrostatic repulsion associated with membrane fixed charge groups as they become ionized. Unlike PMAA, pH-dependent swelling was not observed in PA membranes which do not contain ionizable charge groups. Thus, the hydration of the PA membrane was essentially constant over the entire pH range and nearly the same as the hydration of PMAA (S.05/1) in 100 mM KCl at neutral pH. PMAA disks equilibrated at ~50 mM ionic strength showed 46% greater swelling by pH 7 than identical membranes tested at ~100 mM ionic strength.

EXAMPLE III: Membrane Swelling Kinetics

The kinetics of PMAA membrane swelling were measured over a 58-hour period using disks cut from S.05/1 membranes cast to four different thicknesses: 125, 250, 500 and 1000 μm. After pre equilibration in 50 mM KCl solution at pH 3, the bath pH was changed to 6, held constant for 48 hours, and then returned to pH 3. The wet weight of each disk was measured at various times during this period and the specimen was reimmersed after each measurement (the weighing procedure took less than 3 minutes). Dry weights were measured at the end of the test, to enable calculation of the average hydration of each disk versus time.

Figure 3:
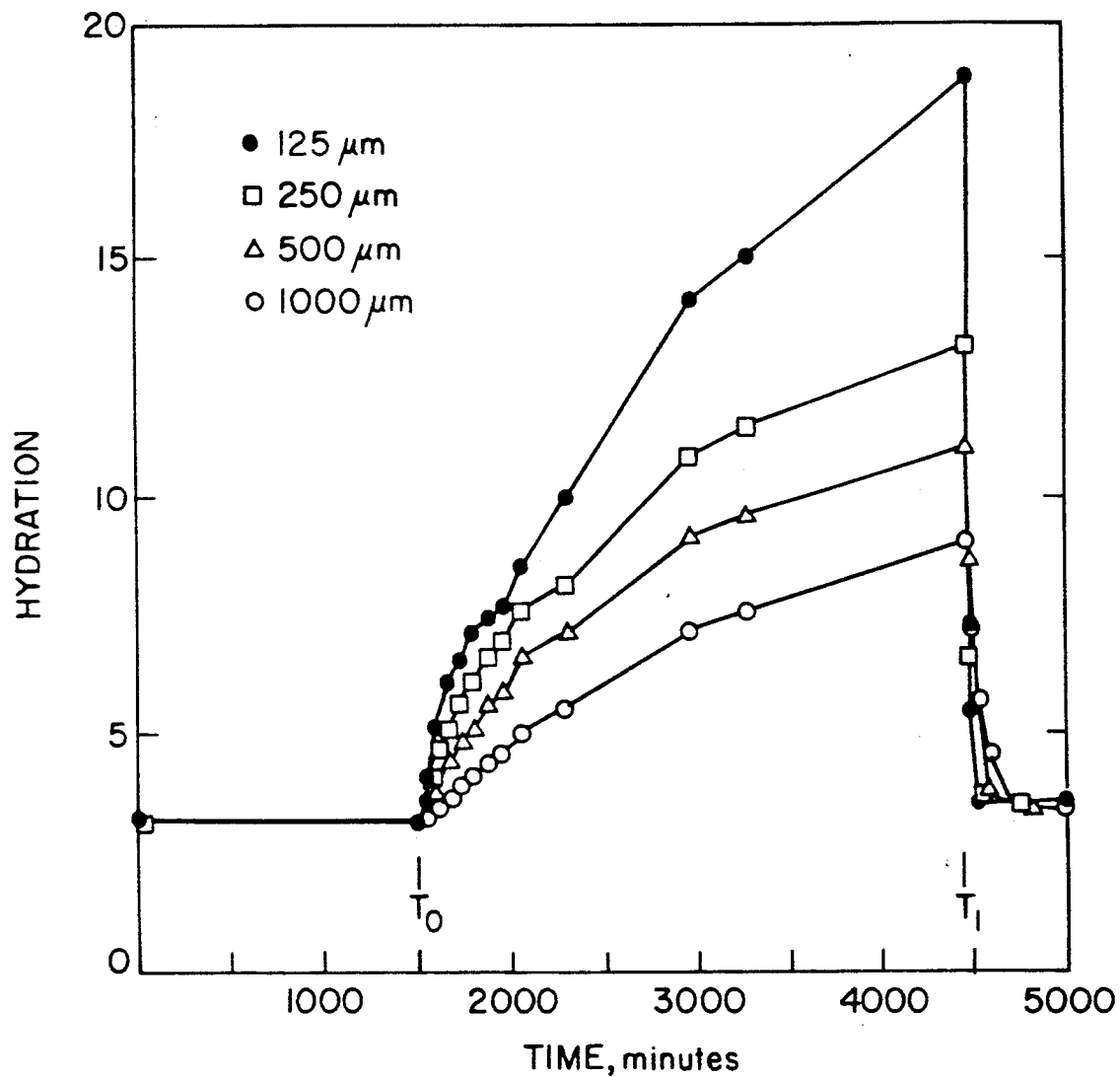
FIG. 3 is a graphic representation of the transient hydration of S.05/1 PMAA membranes in unbuffered 50 mM KCl measured simultaneously for disks from membranes cast to a thickness of 125 $\mu$m (●), 250 $\mu$m (□), 500 $\mu$m (Δ), and 1000 $\mu$m (o). Bath pH was changed from 3 to 6 at time $T_0$ and back to pH 3 at time $T_1$.

FIG. 3 shows the kinetics of swelling of S.05/1 PMAA membrane disks in response to a step increase in bath pH from 3 to 6 (at $T_0$). Each data point corresponds to the mean of three wet weights for that disk. The swelling response was slower for thicker membranes. When the specimens were transferred back to the pH 3 bath at t-4500 minutes ($T_1$), a rapid deswelling was observed. The deswelling was faster with decreasing membrane thickness.

EXAMPLE IV: Solute Characterization

Transport experiments were performed using neutral or charged fluorescent solutes, whose properties are listed in Table 1. N-(3-sulfopropyl) acridinium inner salt (NSPA) (MW 301) was obtained from Molecular Probes, Inc. (Eugene, OR); dextran (MW 10,000) was conjugated to Lissamine-rhodamine B sulfonyl chloride (Lis). These two neutral solutes were chosen since they are water-soluble, pH-insensitive (below pH 7), and photostable. Synthesis of the Lissamine-dextran conjugate (Lis-DEX) (Molecular Probes, Inc.) involved aminating the dextran, reacting with it the fluorophore, and then capping any unreacted amines by treating with acetic anhydride to insure a neutral product. Net neutrality of both of the solutes was confirmed by cellulose acetate electrophoresis.

Fluorescent protein solutes were produced by conjugating anthracene (Anth) and Lissamine-rhodamine B fluorophores, respectively, to ribonuclease A (RNase)(-type XII-A, Sigma Chemical, St. Louis. Mo.) and bovine serum albumin (BSA)(Pentex Monomer standard, Miles Laboratories, Elkhart, Ind.). Due to the difference in their isoelectric points, RNase has a net positive charge and BSA is net negative at pH 7 (Table 1). Richards, F. M., and Wyckoff, H. W., The Enzymes, (Ed. P.

D. Byer) 3rd Edition, pp 647-806. Academic Press. NY, (1971); Peters, T., *Advances in Protein Chemistry*, (Ed. C. B. Antinsen) Vol. 37, pp 161-245, Academic Press, Orlando, Fla., (1985). The sulfonyl chloride form of each fluorophore was dissolved in a minimal volume of solvent (acetonitrile for Lis and acetone for Anth), and reacted with the protein in a 0.1M NaCl-0.75M NaHCO$_3$ buffer (pH 9).

The reaction mixtures were then applied to gel filtration columns (Sephadex G-50 for Anth-RNase and Sephadex G-150 for Lis-BSA) and the reacted and unreacted products were eluted with phosphate-buffered saline. Three $A_{280}$ peaks were identified in each case: the first presumably contained aggregates; the second contained the desired product; and the third contained unreacted dye. Fractions corresponding to the second absorbance peak were dialyzed against water, lyophilized, and stored dry until ready for use. Reverse-phase thin layer chromatogrophy (TLC) (using CH$_3$OH—H$_2$O (70/30) as the developing solvent) and SDS-polyacrylamide gel electrophoresis were used to confirm the absence of free fluorophore in the product.

The fluorophore content of the final product was assessed by making two measurements of the optical density, one at 280 nm where both the protein and fluorophore absorb, and one at a wavelength where only the fluorophore exhibits appreciable absorbance (380 nm for Anth and 575 nm for Lis). The average molar ratio of fluorophore to protein calculated from these measurements was about 2 for Anth-RNase and about 3 for Lis-BSA. (Extinction coefficients for the proteins at 280 nm were taken to be 0.73 ml mg$^{-1}$ cm$^{-1}$ for RNase (Richards, F. M., and Wyckoff, H. W., *The Enzymes*, (Ed. P. D. Byer), 3rd Edition, pps. 647-806, Academic Press NY, (1971)) and 0.66 ml mg$^{-1}$ cm$^{-1}$ for BSA (Yarmush, D. M., et al., *J. Biochem. Biophys. Meth.*, 14:279-289, (1987); extinction coefficients for the free fluorophores, determined from absorbance measures, were 100 ml mg$^{-1}$ cm$^{-1}$ at 280 nm and 12 ml mg$^{-1}$ cm$^{-1}$ at 380 nm for Anth in acetonitrile, and 30 ml mg$^{-1}$ cm$^{-1}$ at 280 nm and 108 ml mg$^{-1}$ cm$^{-1}$ at 575 nm for Lis in phosphate-buffered saline.)

Mean diffusion coefficients were measured by quasielastic light scattering using the 488-nm emission from an argon ion laser and appropriate optical filter to eliminate any solute fluorescence. Yarmush, D. M., et al., *J. Biochem. Biophys. Meth.*, 14:279-289 (1987). The computed hydrodynamic radii ($R_h$) indicated that the addition of fluorophores did not significantly alter the size of the proteins. $R_h$ values were 2.1±0.3 nm (Means±S.D.) for Anth-RNase and 3.3±0.5 nm for Lis-BSA, compared to 1.8±0.3 and 3.5±0.5 nm for unlabelled RNase and BSA, respectively. The latter two values are equivalent to those reported in the literature. Tanford, C., *Physical Chem. of Macromolecule*, John Wiley, NY, (1961); Yarmush, D. M., et al., *J. Biochem. Biophys. Meth.*, 14:279-289 (1987).

TABLE 1

| Fluroescent Solutes Used in Transport Experiments | | | | |
|---|---|---|---|---|
| Neutral Solutes | MW | | Excitation peak (nm) | Emission peak (nm) |
| N-(3-sulfopropyl acridinium) | 301 | | 358 | 488 |
| Lissamine-dextran | 10,000 | | 570 | 590 |
| Protein Solutes | MW* | pI* | $R_H(nm)^{2**}$ | |
| Anthracene-ribonuclease A | 13,700*** | 9.45$^x$ | 2.1 | 360 | 440 |
| Lissamine-bovine serum albumin | 67,000$^{xx}$ | 4.8$^{xx}$ | 3.3 | 570 | 590 |

*M.W. and pI values are for unlabelled proteins
**Hydrodynamic radii were determined by quasi-elastic light scattering
***Hirs et al., J. Biol. Chem., 219: 623-642 (1955)
$^x$Richards and Wyckoff, op. cit., (1971)
$^{xx}$Peters, op. cit., (1985)

EXAMPLE V: Transport Apparatus

In the transport apparatus of these examples, the membrane was supported between two PMAA half cells, each holding 100 ml of bath solution. The area of membrane exposed to the baths was 4.8 cm$^2$. Each bath was stirred and recirculated at a flow rate of 150 $\mu$l/sec by a peristaltic pump, which streamed fluid adjacent to each surface of the membrane to minimize stagnant fluid layers. A DC current source delivered a transmembrane electric field via a pair of salt bridge electrodes placed in the baths. Each electrode consisted of a platinum plate separated from the bath solution by a PA gel salt bridge filled with 2.5M KCl solution.

Solutes were placed in the upstream bath and detected fluorometrically in the downstream bath. To measure downstream concentrations, the solution was circulated through a 0.8-$\mu$m Milli-Fil PF filter (Millipore Corp., Bedford, Mass.) and then through two fluorescence detectors, each tuned to the excitation and emission peaks corresponding to one of the fluorescent solutes (FIG. 1). The fluorescence detectors were a model SPF-500C spectrofluorometer (SLM Instruments, Urbana, Ill.) and a model RF-530 fluorescence monitor (Shimadzu Corp., Kyoto, Japan). In one series of experiments (chemical control of membrane permeability) the data were obtained using a spectrofluorometer and laser-photodiode fluorescence detection system, Weiss, A. M., et al., *AIChE Symp. Ser.*, 82:85-98 (1986).

The temperature and pH of each bath was monitored continuously using a pH meter (model 231, Orion Research, Cambridge, Mass.) equipped with a temperature probe and a Ross combination pH electrode (Orion Research). The two pH meters were electrically isolated from each other and from the ground to eliminate alternate current paths between the two baths. Both baths were maintained at 20° C. by automatically heating with PTFE covered chromel heating wires and cooling through a heat exchanger. Model 665 Dosimat automatic burettes (Metrohm Ltd., Herisau, Switzerland) delivered small volumes of HCl and KOH to each bath to maintain and change the pH as desired.

In the following examples, a membrane was equilibrated in the bath solution overnight and mounted in the transport cell. Solutes were then added to the upstream bath after establishing a zero baseline for the fluorescence detectors. The upstream concentration was approximately 10$^{-5}$M for the neutral solutes. When the protein solutes were used, 0.13-0.24 mg/ml of Anth-RNase and Lis-BSA were added to the upstream bath, and equal concentrations of unlabeled RNase and BSA were placed in the downstream bath. Calibration of the measured fluorescence to the transmembrane concentration difference of labelled solute was done periodically by adding 10-500 μl of the upstream bath to the downstream bath and noting the resultant change in fluorescence. The downstream solute concentration was measured fluorometrically and recorded every 2 seconds via a microcomputer. Potassium azide (3 mM) was routinely used as an anti-bacterial agent in the electrolyte baths.

EXAMPLE VI: Chemical Control of the Membrane Permeability

The effect of changes in membrane hydration on the flux of the neutral solutes NSPA and Lis-DEX was determined using a PMAA (S.4/1) membrane. No electric field was applied. The baths consisted of unbuffered 50 mM KCl, with the downstream bath at pH 5.5-6 and the upstream bath initially at pH 3. After addition of both solutes to the upstream bath and attainment of a steady-state transmembrane flux, the upstream bath pH was raised and maintained between 5.5 and 6. The resulting changes in the solute flux were recorded. After a new steady-state flux was reached for both solutes, the upstream pH was lowered back to 3.

Figure 4:
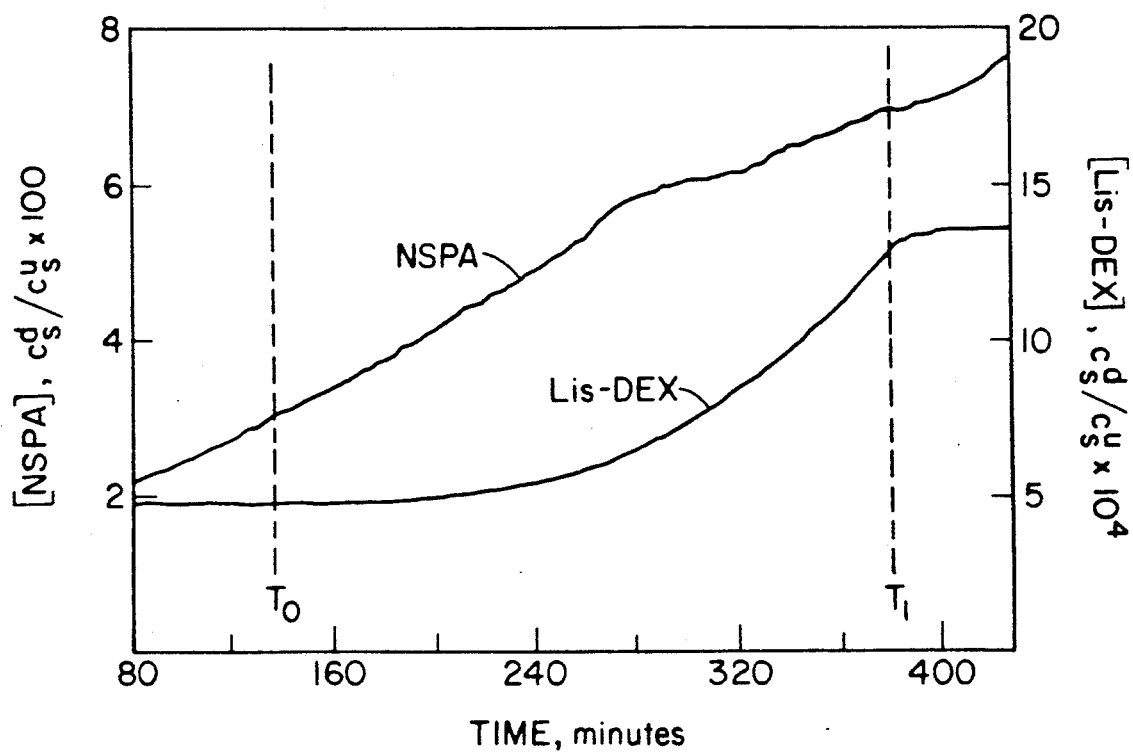
FIG. 4 is a graphic representation of the normalized downstream concentration of NSPA and Lis-DEX versus time for transport across a PMAA (S.4/1) membrane in unbuffered 50 mM KCl baths. The downstream bath was maintained at pH 5.5-6. The upstream pH was changed from 3 to 5 at time $T_0$ and back to pH 3 at time $T_1$.

FIG. 4 shows the effect of changes in bath pH on the magnitude and kinetics of changes in permeability of PMAA S.4/1 membranes to Lis-DEX and NSPA. The data are plotted as the downstream solute concentration ($c^d_s$) normalized to the upstream concentration ($c^M_s$) vs time. Over the intervals where a steady state was reached, the solute flux $\Gamma_s$, was calculated from the slope of the downstream concentration using a linear regression:

$$\Gamma_s = \frac{(\partial c_s^d) V}{(\partial c_s^M) A} \quad (1)$$

where V is volume of the downstream bath, and A is the total exposed membrane area. Based on the regression statistics, the error in the reported flux was always less than 2%. In order to compare the results for membranes having different initial thickness and/or porosity (hydration), it is convenient to define a normalized flux $\Gamma'_s$ as $$\Gamma'_s = \Gamma_s \delta_o / \Phi_o c^M_s \quad (2)$$

where $\delta_o$ is the initial membrane thickness, and $\Phi_o$ is the initial membrane porosity (fraction of fluid area to total membrane area) defined at $H_o/(1+H_o)$. In writing Equation (2), it is assumed that $c^M_s$ does not appreciably change during the experiment, and that $c^M_s$ is greater than $c^d_s$. (This was always the case for the macromolecular solutes, and resulted in an error of less than 8% for the computed flux of NSPA.) Therefore, when diffusion is the only transport mechanism, the normalized flux $\Gamma'_s$ is equal to the effective intramembrane diffusivity of the solute for the initial state of the membrane.

In FIG. 4, time t=80 corresponds to 25 minutes after the addition of Lis-DEX and 48 minutes after the addition of NSPA to the upstream bath. With the downstream bath at pH 5-5.5 and the upstream bath initially at pH 3, an approximately linear increase in NSPA concentration prior to $t=T_0$ suggests that a steady flux was already established, corresponding to a $\Gamma'_s$ of $7.5 \times 10^{-11} m^2/s$. At the same time the downstream Lis-DEX concentration is flat to within the measurement sensitivity, indicating a normalized flux of less than $10^{-14} m^2/s$.

When the pH of the upstream bath was increased to approximately pH 5, there was little change in the transport of NSPA; however after several hours the Lis-DEX slope increased dramatically, giving a final steady $\Gamma'_s$ of $3.9 \times 10^{-12} m^2/s$. When the upstream pH was returned to pH 3, the Lis DEX flux decreased rapidly to $1.5 \times 10^{-13} m^2/s$.

Throughout the test, the NSPA flux changed by less than 50% of its initial value. (Other experiments with the same membranes demonstrated changes in NSPA flux of less than a factor of 2 for similar pH changes.) In contrast, the flux of Lis-DEX changed by a factor of 26 in FIG. 4 (and as high as a factor of 85 in other tests), revealing a selective, reversible change in the permeability of PMAA to a neutral solute (e.g., up to a factor of 45 change in the ratio of NSPA to Lis-DEX flux).

These results indicate that changes in PMAA membrane hydration are accompanied by changes in permeability to neutral solutes. This selective permeability change is consistent with size-specific solute restriction in addition to size independent porosity and tortuosity effects. The qualitative similarity of the kinetics of membrane swelling (FIG. 3) and of changes in permeability to size-restricted solutes (FIG. 4, Lis-DEX) is further, strong evidence of the association between membrane hydration and permeability.

EXAMPLE VII: Electrokinetic Control of the Solute Flux

Four different combinations of neutral and charged membranes with two neutral or charged solutes were used to determine the electrophoretic migration and electroosmotic convection of solutes in the presence of an electric field: (1) NSPA and Lis-DEX across a PA membrane, (2) NSPA and Lis-Dex across a PMAA (S.05/1) membrane, (3) Anth-RNase and Lis-BSA across a PA membrane, and (4) Anth-RNase and Lis-BSA across a PMAA (S.05/1) membrane.

The bath solutions consisted of 100 mM KCl buffered at pH 7 with 1 mM potassium phosphate. Initially no electric field was applied. After two solutes were added to the upstream bath and a steady state flux was attained, a current density of +100 A/$m^2$ was applied across the membrane, (defined as positive in the upstream to downstream direction), and maintained for 20-30 minutes. The current was then shut off for 25-30 minutes and reapplied in the reverse direction for 20-30 minutes. In some tests, the current was reversed without an intervening zero-current period.

(1) NSPA and Lis-DEX across PA membrane

Figure 5:
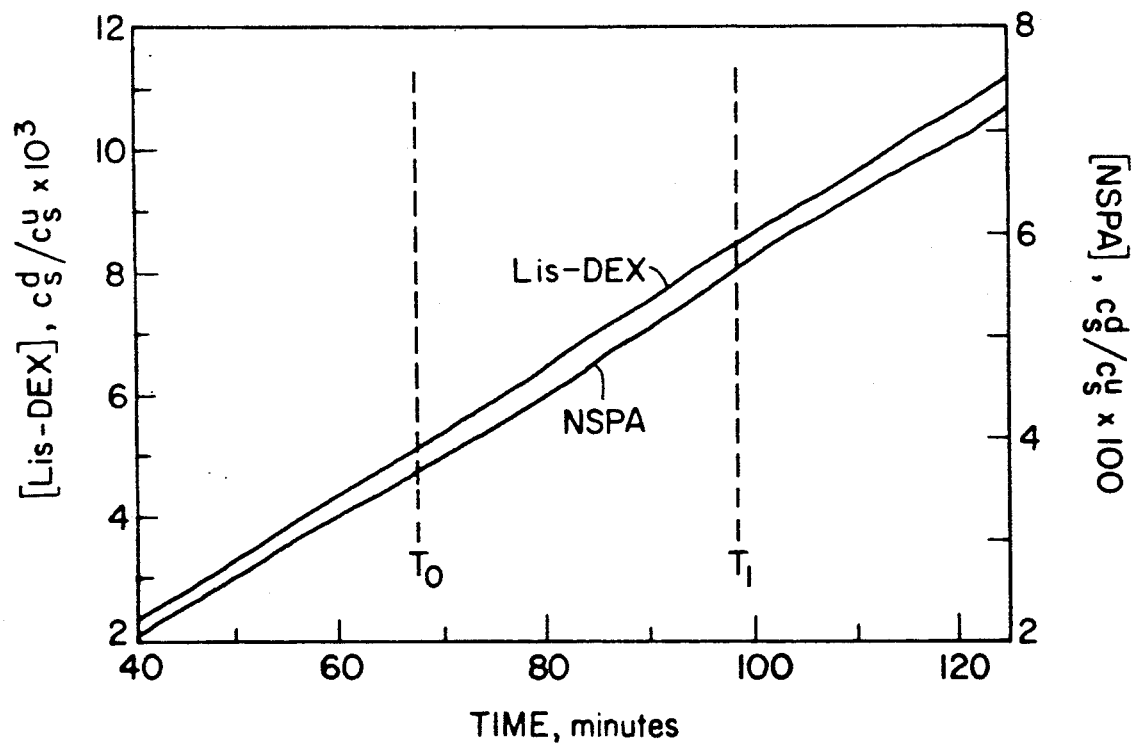
FIG. 5 is a graphic representation of the normalized downstream concentration of NSPA and Lis-DEX versus time, for transport across a PA membrane in 100 mM KCl buffered at pH 7. A current density of +100 A/m$^2$ was applied across the membrane (upstream to downstream) between times $T_0$ and $T_1$. No current was applied for $t < T_0$ or $t > T_1$.

FIG. 5 shows that an applied current had essentially no effect on the transport of the neutral solutes across the neutral PA membrane. The normalized flux of NSPA flux changed from $2.0 \times 10^{-10} m^2/s$ when a current density of +100 A/$m^2$ was applied at $t=T_0$ and to $1.9 \times 10^{-10} m^2/s$ when the current was turned off at $t=T_1$. The flux of Lis-DEX (measured simultaneously) changed from $3.5 \times 10^{-11}$ to $3.6 \times 10^{-11} m^2/s$ with the same positive current, and then to $3.4 \times 10^{-11} m^2/s$ with no current. These pre- and post-field flux values are summarized in Table 2, along with the data from the electrokinetic experiments of FIGS. 6-8.

(2) NSPA and Lis-DEX across PMAA membrane

Figure 6:
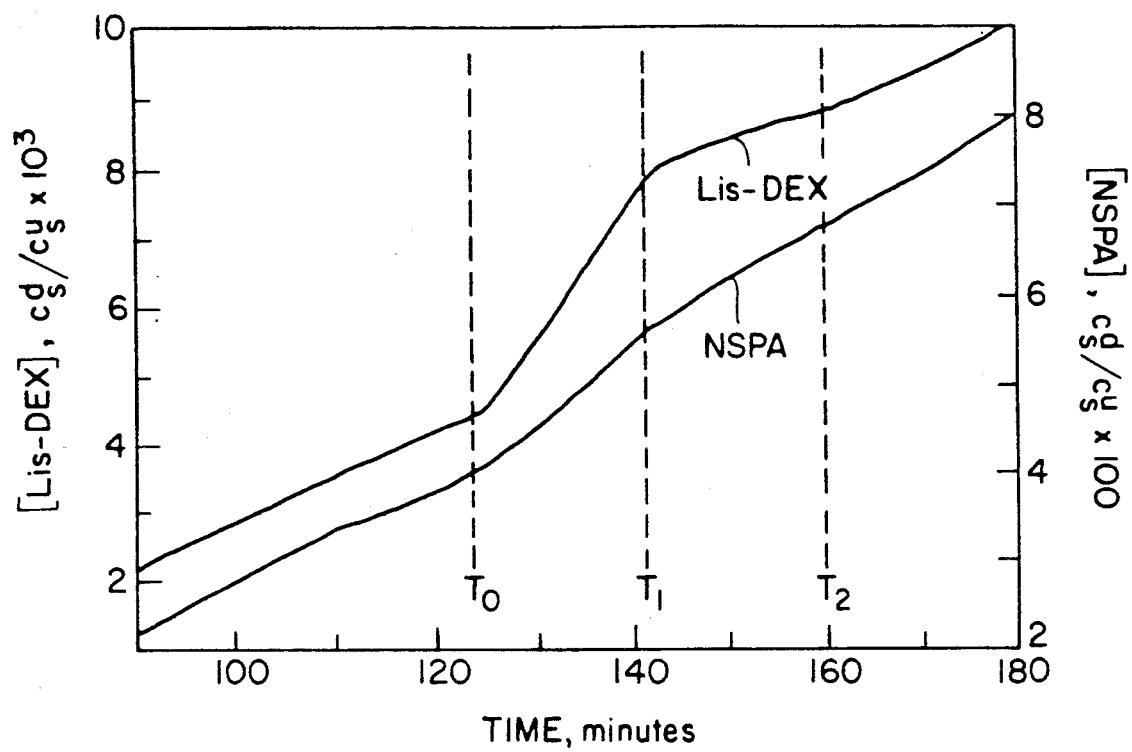
FIG. 6 is a graphic representation of the normalized downstream concentration of NSPA and Lis-DEX versus time, for transport across a PMAA (S.05/1) membrane in 100 mM KCl buffered at pH 7. +100 A/m$^2$ was applied across the membrane starting at time $T_0$. The current polarity was reversed at time $T_1$; the current was removed at time $T_2$.

The experiment of FIG. 5 was repeated using a charged PMAA (S.05/1) membrane. Under these conditions, the flux of neutral solutes was enhanced or depressed by the applied field, depending on its polarity. For a given current density, the change in the flux was larger for the larger Lis-DEX solute. In the experiment of FIG. 6, for example, +100 A/m$^2$ applied at $t=T_0$ increased the flux of NSPA by 66%, while the flux of Lis-DEX increased by a factor of 3.2 (Table 2). Reversing the direction of the current decreased the NSPA flux slightly below its initial value and decreased the flux of Lis-DEX to 64% of its initial zero-current value.

In the experiment of FIG. 6, the electroosmotic augmentation of solute flux was proportional to the magnitude and direction of the applied current density at pH 7 and was greatly reduced after neutralization of the PMAA fixed charges at pH 3. As was observed, solute convection added to the diffusive flux when a positive current was applied, and opposed the diffusive flux when the current reversed. Since Lis-DEX has a lower diffusivity and hence a larger Peclet number within the membrane, the solvent flux would be expected to have a greater effect on the Lis DEX flux.

(3) Anth-RNase and Lis-BSA across PA membrane

Figure 7:
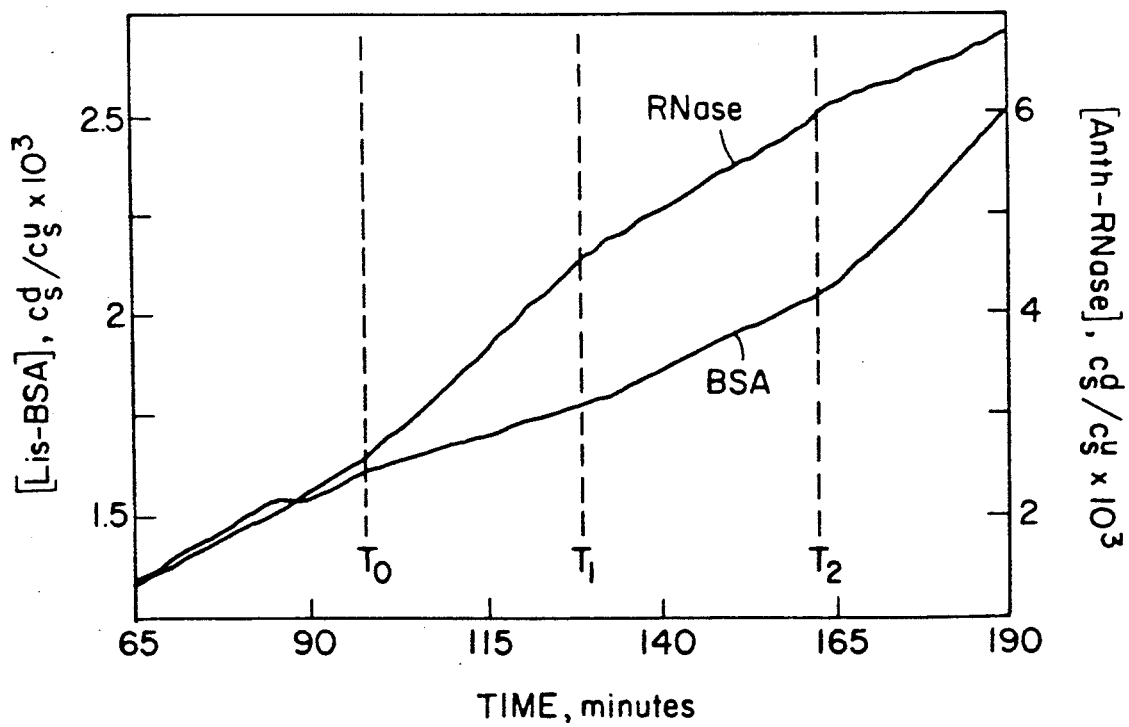
FIG. 7 is a graphic representation of the normalized downstream concentration of Lis-BSA and Anth-RNase versus time, for transport across a PA membrane in 100 mM KCl buffered at pH 7. +100 A/m$^2$ was applied across the membrane at time $T_0$. The current was removed at time $T_1$, and reversed at time $T_2$ (−100 A/m$^2$).

The experiment of FIG. 5 with neutral PA membranes was again repeated, but this time using the protein solutes. The results demonstrated that protein flux could be significantly altered by an applied electric field. In the experiment of FIG. 7, application of +100 A/m$^2$ at $t=T_0$ increased the normalized flux of positively charged Anth-RNase by 72% and decreased the flux of negatively charged Lis-BSA to 60% of its initial value (Table 2). After the current was turned off at $t=T_1$, the fluxes returned to near their initial levels. Reversal of the current to −100 A/m$^2$ at $t=T_2$ reduced the Anth-RNase flux to 73% of its initial zero-current value and increased the Lis-BSA flux to double its initial value.

In the experiment of FIG. 7, there are no gradients in bath pH or ionic strength across the membrane, and electroosmosis is absent since the PA membrane is neutral. An electrophoretic mechanism is consistent with the increased flux of positive RNase and the decreased flux of negative BSA in response to a positively directed current. In addition, the changes in flux reversed when the current direction was reversed. The charge specificity of this transport mechanism provides an additional basis for membrane-based, electrically controlled protein separation.

(4) Anth-RNase and Lis-BSA across PMAA membrane

Figure 8:
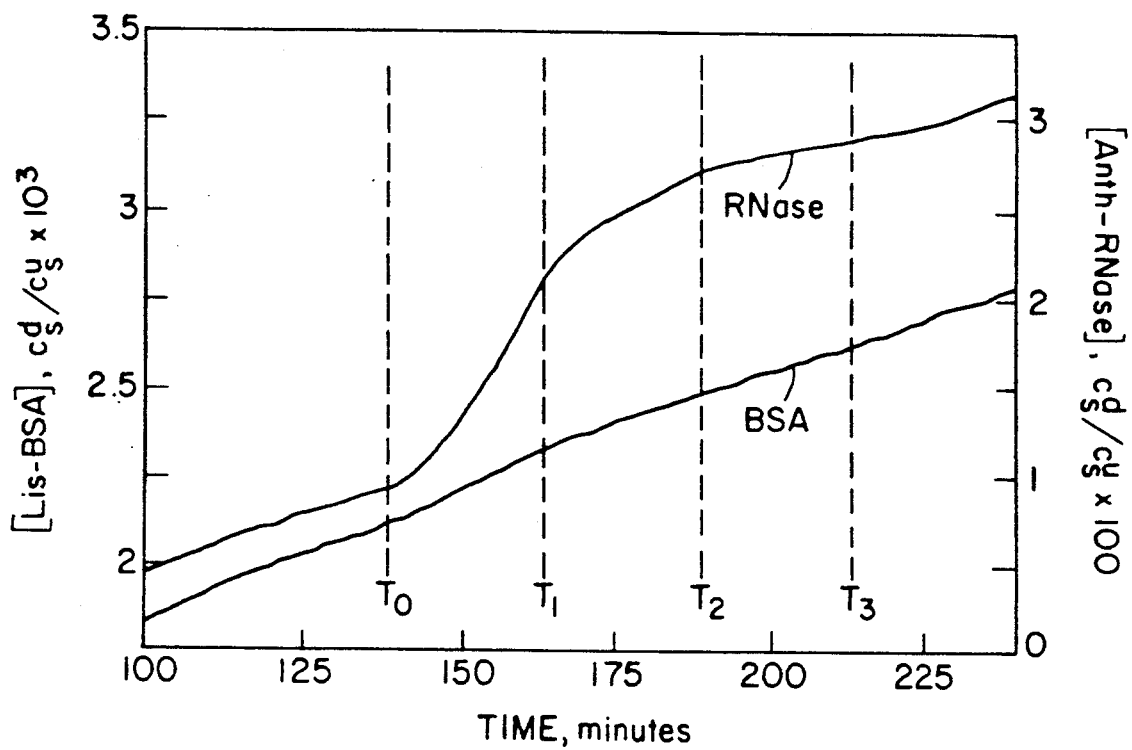
FIG. 8 is a graphic representation of the normalized downstream concentration of Lis-BSA and Anth-RNase versus time, for transport across a PMAA (S.05/1) membrane in 100 mM KCl buffered at pH 7. +100 A/m$^2$ was applied across the membrane at time $T_0$. The current was removed at time $T_1$, reversed at time $T_2$ (−100 A/m$^2$), and removed at time $T_3$.

FIG. 8 shows the effect of an electric field on the transport of charged proteins across a charged PMAA (S.05/1) membrane. Application of +100 A/m$^2$ at $t=T_0$ resulted in a marked increase in the normalized flux of Anth-RNase by a factor of 5.2. However, the flux of Lis-BSA increased only slightly (Table 2). When the current was shut off at $t=T_1$, the Lis-BSA flux decreased to slightly less than its pre-field value, and the flux of Anth-RNase did not completely return to its pre-field value in the time allowed. With negative current applied at $t=T_2$, both fluxes decreased below their initial values (Table 2).

In the experiment of FIG. 8, the applied current induces both electrophoretic and electroosmotic solute transport. The five-fold increase in the RNase flux at $t=T_0$ with +100 A/m$^2$ resulted from the additive contributions of the two mechanisms. With oppositely charged BSA, the electrophoretic and electroosmotic contributions opposed each other, consistent with the much smaller change in the flux at $t=T_0$. The result was a four-fold increase in the selectivity (ratio of protein fluxes after stimulation relative to the initial ratio) to RNase over BSA in response to the current. The slow recovery of the RNase flux after cessation of the current may indicate solute-membrane interactions which could lengthen the characteristic diffusion time. The greater in the RNase flux compared to BSA upon reversal of the current at $t=T_2$ is evidence of a combined electroosmotic and electrophoretic effect.

TABLE 2

| | | Electrokinetic Control of Solute Flux | | | |
| | | Normalized flux: $\Gamma'_2$(m$^2$/s) | | | |
| Membrane | Solute | Pre-Field | +100 A/m$^2$ | Post-field | −100 A/m$^2$ |
| --- | --- | --- | --- | --- | --- |
| (1)PA (FIG. 5) | NSPA | 2.0 × 10$^{-10}$ | 2.1 × 10$^{-10}$ | 1.9 × 10$^{-10}$ | |
| H = 18, $\delta_o$ = 93 μm | Lis-DEX | 3.5 × 10$^{-11}$ | 3.6 × 10$^{-11}$ | 3.4 × 10$^{-11}$ | |
| (2)PMAA(FIG. 6) | NSPA | 3.8 × 10$^{-10}$ | 6.3 × 10$^{-10}$ | | 3.7 × 10$^{-10}$ |
| H = 20, $\delta_o$ = 181 μm | Lis-DEX | 4.4 × 10$^{-11}$ | 1.4 × 10$^{-10}$ | | 2.8 × 10$^{-11}$ |
| (3)PA (FIG. 7) | Anth-RNase | 2.2 × 10$^{-11}$ | 3.8 × 10$^{-11}$ | 2.3 × 10$^{-11}$ | 1.6 × 10$^{-11}$ |
| H = 18, $\delta_o$ = 155 μm | Lis-BSA | 4.9 × 10$^{-12}$ | 2.9 × 10$^{-12}$ | 4.6 × 10$^{-12}$ | 1.0 × 10$^{-11}$ |
| (4)PMAA(FIG. 8) | Anth-RNase | 7.3 × 10$^{-11}$ | 3.8 × 10$^{-10}$ | 1.2 × 10$^{-10}$ | 3.7 × 10$^{-11}$ |
| H = 20, $\delta_o$ = 181 μm | Lis-BSA | 4.5 × 10$^{-12}$ | 5.6 × 10$^{-12}$ | 4.0 × 10$^{-12}$ | 3.6 × 10$^{-12}$ |

EXAMPLE VIII: Electroosmotic Solvent Flux

In order to directly measure the solvent flux caused by electroosmosis in the PMAA membranes, S.05/1 PMAA membranes were mounted in an apparatus similar to that used in the transport experiments. The two baths of 100 mM KCl were open to the atmosphere through thin volumetric pipets. Exposed membrane area was 3.1 cm$^2$. With both baths at pH 7, a transmembrane current density of 320 A/m$^2$ was applied first in one direction, turned off, then applied in the opposite direction, and finally reduced to 120 A/m$^2$. The pH of both baths was lowered to 3; after re-equilibration of the membrane, a current density of 320 A/m$^2$ was applied. Volume flux across the membrane was measured by recording the fluid level in the pipets at 1 second intervals. In a separate experiment, steady-state electroosmotic solvent flux was measured before and after the addition of 13 mg/ml RNase and 15 mg/ml BSA to both baths in order to detect possible membrane L fouling by the proteins.

The current density J of 320 A/m$^2$ applied across S.05/1 PMAA membranes at pH 7 induced a solvent flux of 1.2×10$^{-6}$m/s in the direction of the applied current; reversal of the current led to a flux of 1.1 ×10⁻⁶m/s in the opposite direction. When the current density was reduced to 120 A/m², the solvent flux dropped to 3.5×10⁻⁷m/s. Using these data, the average electroosmotic coupling coefficient ($k_j$) was U/J=3.2×10⁻⁹m³/A s at pH 7. When the pH was decreased to 3, the solvent flux was greatly reduced 4.5×10⁻⁸m/s) in response to a 320-A/m² current density. No significant change in electroosmotic solvent flux was noted after the addition of RNase and BSA in the concentrations used in the transport experiments.

Non-specific electrostatic interactions will affect the equilibrium partitioning of charged solutes across each interface of a charged membrane. For PMAA membranes negatively charged at pH 7, the upstream concentration of positively charged RNase just inside the membrane would be higher than that in a neutral membrane, all other conditions being equal. This is consistent with the enhanced RNase flux observed across PMAA prior to application of the field compared to the pre-field RNase flux across the neutral PA membrane (Table 2). Conversely, the pre field flux of BSA was less across PMAA than PA. The resulting selectivity to RNase over BSA was greater compared to neutral membranes of similar hydration. (Of course, different membranes having equal hydration may exhibit differences in size specificity.) Thus the data suggest that varying solute and/or membrane charge in order to modulate electrostatic partitioning provides an additional mechanism for separating and controlling the flux of charged solutes.

Figure 9:
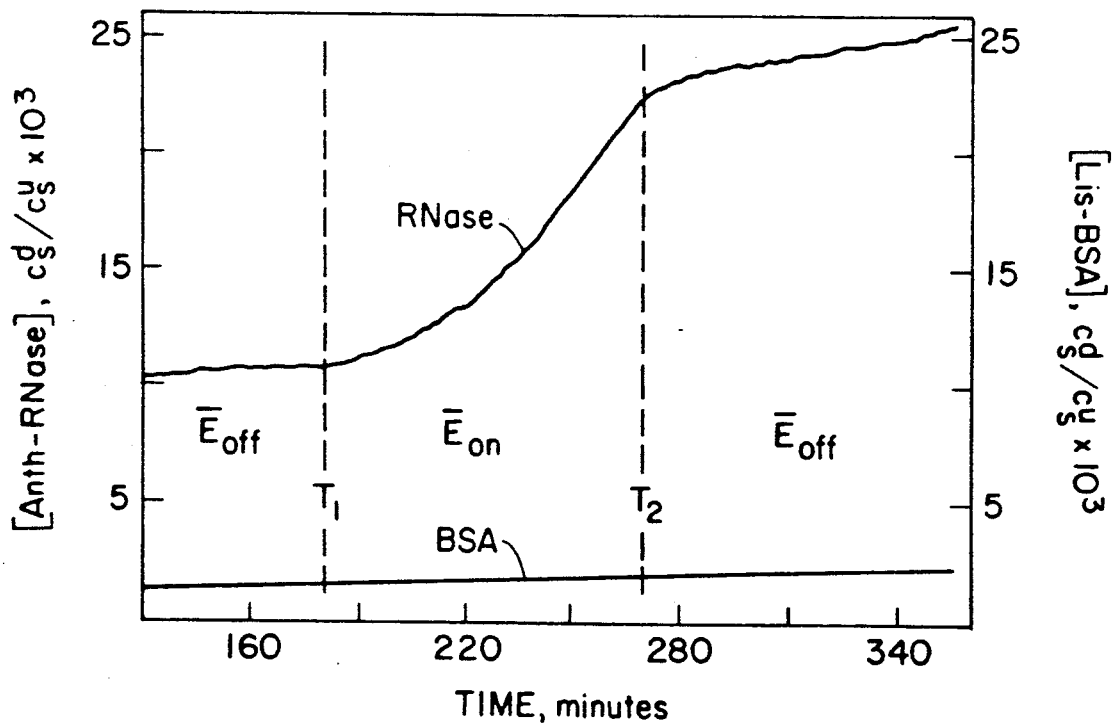
FIG. 9 is a graphic representation of the normalized downstream concentration of Lis-BSA and Anth-RNase versus time, for transport across a PMAA membrane in 100 mM KCl with 5 mM imidazol. The pH of the bath was lowered from 7 to 5.5 at $t = T_0$. +100 A/m$^2$ was applied across the membrane from time $t = T_1$ to $t = T_2$.

EXAMPLE IX: Interaction of Electrophoresis, Electroosmosis, Electromechanical Deformation and Electrostatic Partitioning A final transport experiment was run using the protein solutes to determine the effect on solute flux of adding electrophoresis to the electrically induced swelling and electroosmotic phenomena already demonstrated with neutral solutes. FIG. 9 shows changes in the flux of Anth-RNase and Lis-BSA across an S.05/1 PMAA membrane in 100 mM KCl with 5 mM imidazol. Both of the proteins were placed in the upstream bath in this experiment. Both the upstream and downstream baths were maintained at pH 7 for t<$T_0$ in FIG. 9, leading to a steady-state flux of 8.5×10⁻¹¹m²/s for Anth-RNase and 3.3×10⁻¹²m²/s for Lis-BSA.

When the pH of the downstream bath was lowered to 5.5 at t=$T_0$, the Anth-RNase flux decreased to 5.7×10⁻¹²m²/s, while the Lis-BSA flux fell only slightly to 2.9×10⁻¹²m²/s. After application of 100 A/m² (upstream to downstream) at t-$T_1$, the flux of Anth-RNase increased slowly by a factor of 24 to 1.4×10⁻¹⁰m²/s; it subsequently decreased back to 1.7×10⁻¹¹m²/s when the field was turned off at time $T_2$.

The large change in Anth-RNase flux was accompanied by a relatively small (11%) increase in Lis-BSA flux when the field was applied, followed by a 31% drop after the field was turned off. The resulting 21-fold increase in selectivity to RNase over BSA measured here due to the applied field demonstrates the use of a combination of mechanisms for selective, reversible control of protein flux across PMAA membranes.

The use of the protein solutes in the above pH-gradient experiment involves the additional mechanisms of electrophoresis and electrostatic partitioning. The 24-fold electrically induced increase of RNase flux versus the relatively insignificant 11% change in BSA flux demonstrates the potential selectivity that can be obtained in a membrane separation using a combination of the four electromechanical control mechanisms (i.e., electrophoresis, electroosmosis, electrostatic partitioning, electromechanical deformation).

Since the transport of both RNase and BSA was from the upstream to the downstream bath in this experiment, the effects of electroosmosis and electrically induced swelling were additive for both proteins. Electrophoresis, however, would enhance the transport of RNase and oppose that of BSA (for intramembrane pH above its pI of 4.8), and thereby must be at least partially responsible for the observed change in selectivity. In addition, the increased membrane fixed charge density during electrodiffusion would enhance the partitioning of positive RNase within the membrane; at the same time electrostatic exclusion of BSA would increase as both the membrane and the BSA become more negative at higher intramembrane pH.

The pH-gradient experiments demonstrate that electrically induced swelling can contribute to changes in solute flux beyond those produced by electrokinetic mechanisms in membranes of uniform pH. The kinetics of these changes in flux implicate electrodiffusion as the dominant mechanism: during large electrically induced flux changes the turning-on transient was generally slower than the turning-off transient, consistent with observed electrically induced swelling and simulations of swelling induced by electrodiffusion or electrodiffusion accompanied by electroosmosis. (Similar kinetics of flux changes were observed when intramembrane pH was changed by direct chemical means rather than by electrodiffusion). Electrodiffusion influences the solute flux in these experiments not only through membrane swelling, but also via changes in the electroosmotic and electrophoretic parameters initiated by intramembrane pH changes associated with electrodifffusion.

EXAMPLE X: Electrically Controlled Membrane Separation Processes

The electrical control of solute flux across deformable polyelectrolyte membranes can be described via a combination of the following mechanisms:

Electrodiffusion: Augmentation of intramembrane ionic concentrations arises from migration of ions due to an electric field within the membrane, as described in Equation (A1).

$$\Gamma_i = \phi\left(-\overline{D}_i \frac{\partial \overline{c}_i}{\partial x} + \overline{\mu}_i \frac{z_i}{z_i} c_i E\right) + \overline{c}_i U \qquad (A1)$$

The changes in membrane hydration and effective pore size due to the resulting modification of electrostatic swelling forces are summarized by the dependence of the equilibrium hydration $H_{eq}(\overline{c}_i)$ on ionic concentrations in Equation (A9).

$$p(\psi,t) = -M \frac{H(\psi,t) - H_{eq}(\overline{c}_i)}{1 + H_{eq}(\overline{c}_i)} \qquad (A9)$$

Electrophoresis: Electrophoretic transport of charged solutes within the membrane is described by the migration term $\mu_s$, $\overline{c}_s$, $E$ in the solute flux equation written as the sum of diffusion, electrophoretic and electroosmotic components (A11).

$$\Gamma_s = \phi\left(-\overline{D}_s \frac{\partial \overline{c}_s}{\partial x} + \overline{\mu}_s \overline{c}_s E\right) + W_s \overline{c}_s U \quad \text{(A11)}$$

Electroosmosis: Fluid flow U within the membrane arising from electroosmosis is represented by the term $z_m \overline{c}_m FE$ in Darcy's law which describes the relation between membrane hydration and the forces and flows that can modulate hydration (A7).

$$U = -k'\left(\frac{\partial P}{\partial x} + z_m \overline{c}_m FE\right) \quad \text{(A7)}$$

This results in electroosmotic augmentation of solute flux via the convection term $W_s \overline{c}_s U$ in the solute flux equation (A11).

Electrostatic partitioning: Partitioning of charged macrosolutes within the charged membrane can be described by an equilibrium partition condition across the membrane-bath interface, similar to the Donnan equilibrium for ions (A6).

$$\left(\frac{\overline{c}_{i+}}{c_{i+}}\right)^{1/|z_i+|} = \left(\frac{\overline{c}_{j-}}{c_{j-}}\right)^{1/|z_j-|} \quad \text{(A6)}$$

The remaining continuity, electroneutrality, constitutive laws and equation of motion represent the coupling between electrostatic forces, membrane hydration and solute transport, and must be solved simultaneously (See Appendix A). This model can be used to determine suitable operating conditions for a protein separation process employing electrically controlled membranes involving the following steps:

Measurement of the Parameters of the Model

Characterization of membrane charge groups: The equilibrium dissociation constant K and concentration of ionizable fixed charge groups $\overline{c}_{mo}$ are required to predict membrane charging behavior with changes in pH or ionic strength. (For the carboxylic acid groups of our PMAA membranes K was determined by titration and $\overline{c}_{mo}$ was determined from the chemical properties of PMAA.)

Characterization of membrane mechanical properties: The equilibrium membrane hydration modulus M, and hydraulic permeability k' are functions of the ionic environment (pH and ionic strength) which are determined empirically for the particular membrane formulation used.

Characterization of solute transport properties within the membrane: The intramembrane diffusivity $\overline{D}_s$, and electrophoretic mobility $\overline{\mu}_s$, depend both on the effective membrane pore size, itself a function of the membrane hydration state, and the particular solutes of interest. The dependence of $\overline{D}_s$ and $\overline{\mu}_s$ on the membrane hydration state can be determined empirically for each solute, since $\overline{D}_s$ and $\overline{\mu}_s$ will be sensitive to the solute size relative to the effective membrane pore size. The electrophoretic mobility $\overline{\mu}_s$ will also be a function of the solute charge, so it is necessary to characterize the solute charge versus pH by a titration procedure, if not available in the literature.

Prediction of solute flux

The time-varying flux $\Gamma_s$ of each solute across the membrane can be predicted by solving the coupled set of differential equations (A1)–(A11) given the operating conditions, i.e., the bath pH and ionic strength and the time-varying electric current density J applied across the membrane. Solute-selective changes in flux due to changes in current density and/or bath conditions can then be predicted. Hence the model can be used to design procedures for real time control of solute flux and separation.

Separation of a particular solute

In a separation process one could maximize the flux of the desired product across the membrane while suppressing the flux of undesired impurities; alternatively one could restrict the passage of the desired product while allowing the impurities to pass through the membrane. In the above described examples, an electric field was used to enhance the separation of RNase from a binary mixture of BSA and RNase. In this case the operating pH regime was such that the BSA was negatively charged and RNase had a positive charge; the direction of the field were chosen to favor transport of the smaller, positively charged RNase and to have a minimal net effect on the transport of the larger, negatively charged BSA. Within certain practical limiting constraints (e.g., on the pH range or current density) the model could be used predictively to choose operating conditions which maximize, for instance, the relative change in RNase flux versus BSA flux to achieve a more effective separation when the current is applied.

Figure 10:
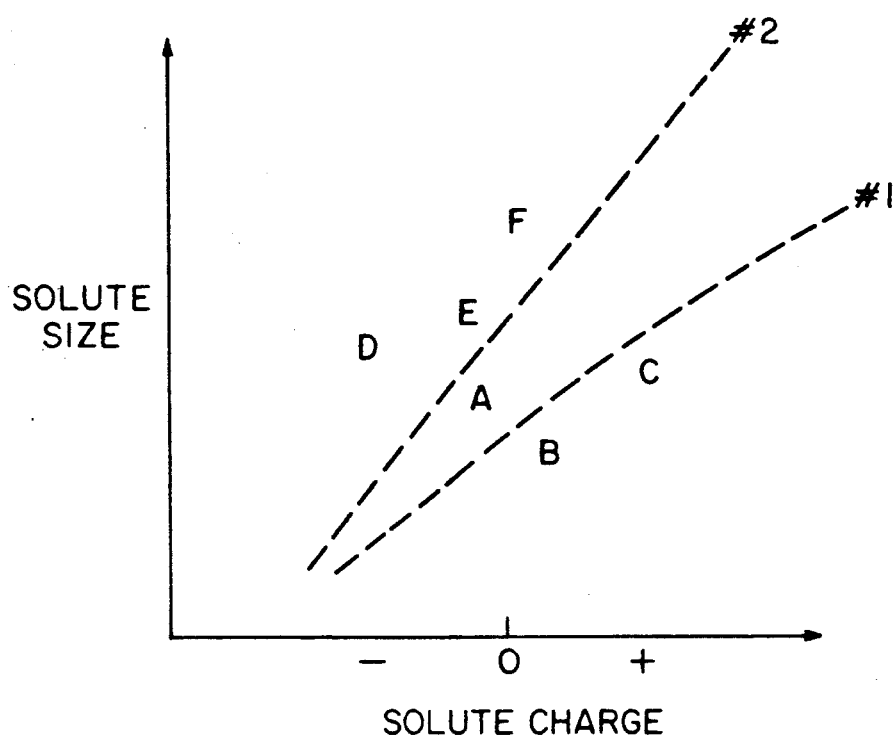
FIG. 10 is a graphic representation of a hypothetical serial elution of component A from a mixture of components A-F.
Figure 11:
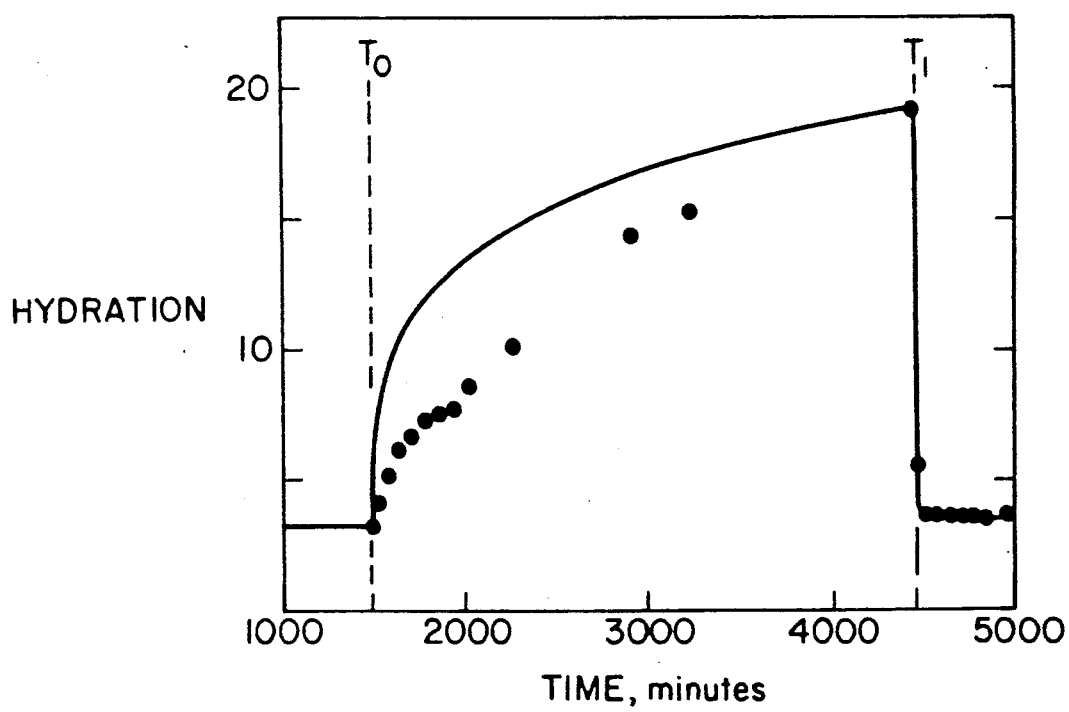
FIG. 11 is predicted and measured transient hydration behavior of PMAA membranes cast to a thickness of 125 $\mu$m in response to a step change in bath pH from 3 to 6 at time $T_0$ and back to pH 3 to time $T_1$.
Figure 12:
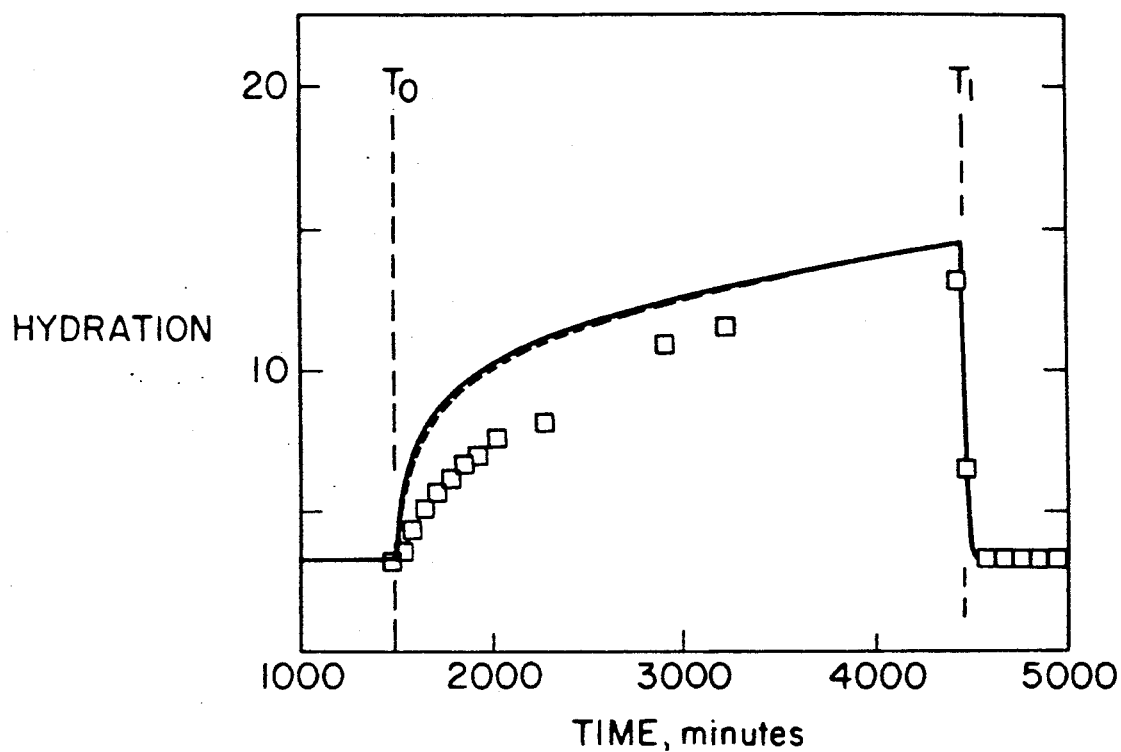
FIG. 12 is predicted and measured transient hydration behavior of PMAA membranes cast to a thickness of 250 $\mu$m in response to a step change in bath pH from 3 to 6 at time $T_0$ and back to pH 3 to time $T_1$.
Figure 13:
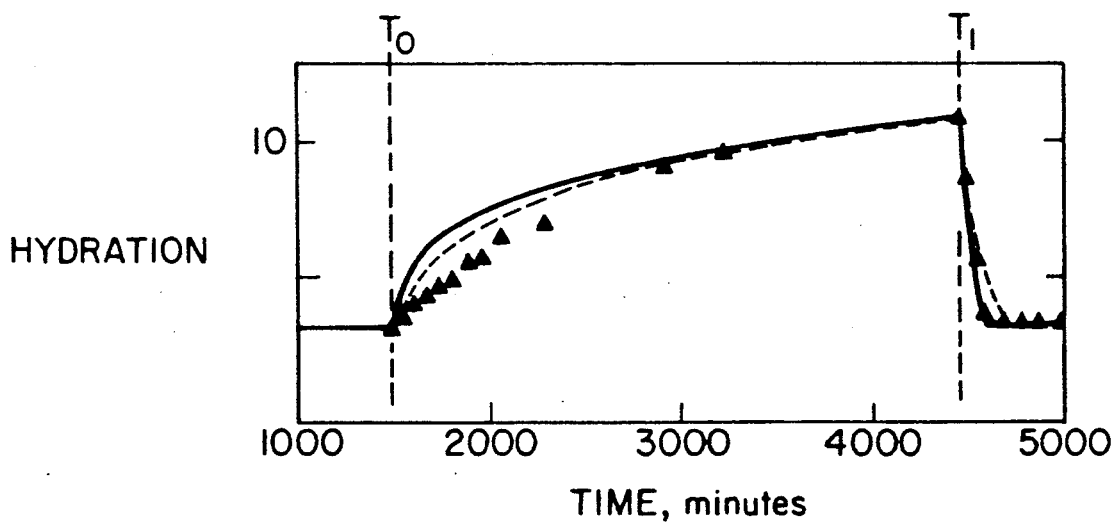
FIG. 13 is predicted and measured transient hydration behavior of PMAA membranes cast to a thickness of 500 $\mu$m in response to a step change in bath pH from 3 to 6 at time $T_0$ and back to pH 3 to time $T_1$.
Figure 14:
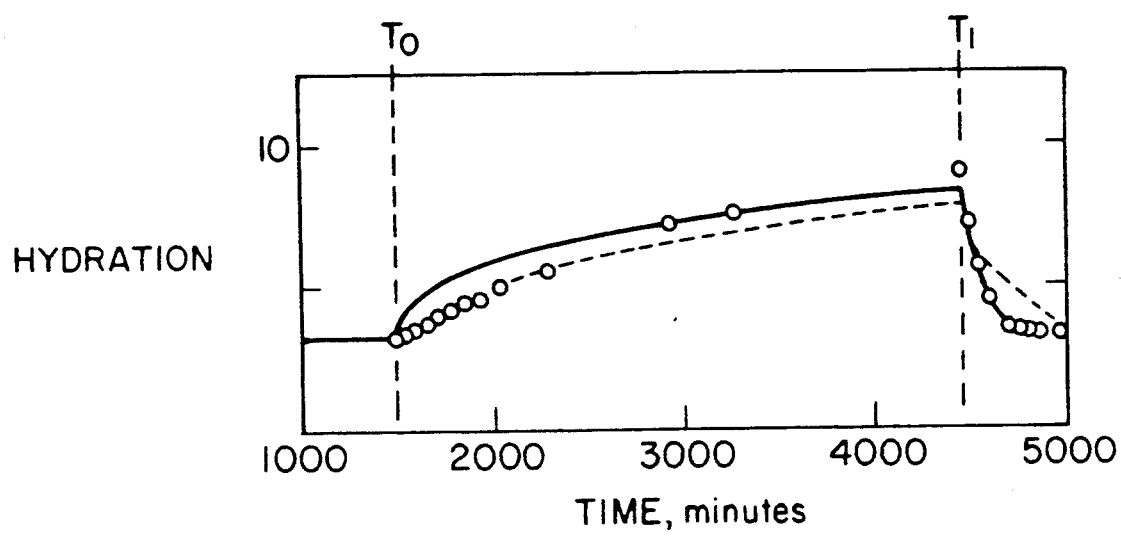
FIG. 14 is predicted and measured transient hydration behavior of PMAA membranes cast to a thickness of 1000 $\mu$m in response to a step change in bath pH from 3 to 6 at time $T_0$ and back to pH 3 to time $T_1$.

Separation of a particular solute from a complex mixture might require a different strategy. A serial elution of components of the mixture from an upstream to a downstream bath could be achieved by continuous or stepwise adjustment of membrane operating conditions. For example, in the hypothetical case shown in FIG. 10, one may want to separate solute A from a mixture of solutes of varying size and charge. Solutes B and C could first be transported across the membrane and removed by setting the membrane operating conditions to obtain an effective "cutoff" shown by the dotted line #1. Then the operating conditions could be changed to "cutoff" line #2 to allow the desired product to pass through the membrane, while retaining solutes D, E and F.

Appendix A

Kinetics of Controlled Changes in Flux

An understanding of the kinetics associated with the examples of FIGS. 3–8 is essential to confirm the underlying mechanisms. A one-dimensional continuum model has been formulated to describe changes in the hydration of polyelectrolyte membranes in response to transmembrane electric fields and changes in ionic environment. Nussbaum, J. H., PhD Thesis, MIT, EECS, (1986); Nussbaum, J. H. and Grodzinsky, A. J., *AIChE*, New York, p. 172D, (1987). This model is intended to include the mechanisms exploited here to control membrane transport and swelling, as well as other phenomena such as electrodiffusion. In this appendix, the predicted kinetics of swelling will be compared to the data of FIG. 3 and the observed kinetics of changes in transmembrane flux.

Electrochemical Equations

The flux of the ith neutral salt or pH-determining ion within the membrane, including diffusion, migration and convection, is $$\Gamma_i = \phi\left(-\overline{D}_i \frac{\partial \overline{c}_i}{\partial x} + \overline{\mu}_i \frac{z_i}{|z_i|} \overline{c}_i E\right) + \overline{c}_i U \quad (A1)$$

where $\overline{c}_i$ is the intramembrane concentration of ion i having effective intramembrane diffusivity $\overline{D}_i$, electrical mobility $\overline{\mu}_i$ and valence $z_i$, $\Phi$ is the membrane porosity, E is the local electric field and U is the total area-averaged fluid velocity relative to the solid. The transmembrane current density J is related to $\Gamma_i$ by the Faraday constant F:

$$J = F \Sigma z_i \Gamma_i \quad (A2)$$

Each ionic species must satisfy the continuity condition $$\frac{\partial}{\partial t}(H\overline{c}_i + H\overline{c}_i^b) = -\frac{\partial(\alpha \Gamma_i)}{\partial \psi} \quad (A3)$$

where $\psi$ is the Lagrangian coordinate frame associated with the solid membrane matrix, $\alpha$ is the total membrane area normalized to its zero-hydration area, H is the local membrane hydration and $\overline{c}^b_i$ is the concentration of ion i reversibly bound to the membrane carboxyl groups (e.g., H+ ions). The concentration of ionized carboxyl groups $\overline{c}_m$, is assumed to follow a Langmuir isotherm:

$$\overline{c}_m = \frac{\overline{c}^s_{mo}}{H} - \overline{c}_H^b = \frac{\overline{c}^s_{mo}}{H}\left(\frac{K}{K + \overline{c}_H}\right) \quad (A4)$$

where K is the equilibrium dissociation constant and $\overline{c}^s_{mo}$ is the carboxyl group density in moles per m$^3$ of solid PMAA. Electroneutrality requires that the sum of the concentrations of the fixed charge and the mobile ionic charge be zero at each position:

$$z_m \overline{c}_m + \Sigma z_i \overline{c}_{\text{,ovs}}/\overline{c}/_i = 0 \quad (A5)$$

The boundary concentrations for each ionic species just inside the membrane (c) are related to the external bath concentrations (c) by the Donnan equilibrium partition conditions:

$$\left(\frac{c_{i+}}{\overline{c}_{i+}}\right)^{1/|z_{i+}|} = \left(\frac{\overline{c}_{j-}}{c_{j-}}\right)^{1/|z_{j-}|} \quad (A6)$$

Electromechanical Equations

The relation between membrane hydration and the forces and flows that can modulate hydration begins with Darcy's law, which describes the fluid flow relative to the solid membrane matrix:

$$U = -k'\left(\frac{(\partial P)}{(\partial x)} + z_m \overline{c}_m F E\right) \quad (A7)$$

where the hydraulic permeability k' may depend on hydration. Fluid can be driven by a gradient in fluid pressure ($\partial P/\partial x$) or by the electric field E (via the electroosmotic term $z_m \overline{c}_m FE$). Osmosis due to steric hindrance of macrosolutes has been neglected here, since large gradients in the concentration of macrosolutes are not imposed in the experiments of interest. Fluid volume satisfies the continuity condition $$\frac{\partial H}{\partial t} = -\frac{\partial(\alpha U)}{\partial \psi} \quad (A8)$$

For the purposes of this discussion, the membrane swelling stress $p(\psi,t)$ is represented by an empirical constitutive law relating p to the hydration H, the equilibrium hydration $H_{eq}(\overline{c}_i)$, and the equilibrium bulk longitudinal modulus of the gel, M:

$$P(\psi, t) = -M\frac{H(\psi, t) - H_{eq}(\overline{c}_i)}{1 + H_{eq}(\overline{c}_i)} \quad (A9)$$

$H_{eq}(\overline{c}_i)$ in Equation (A9) is the hydration that corresponds to equilibrium conditions for a given set of local $\overline{c}_i$; the equilibrium modulus M may vary with $H_{eq}$. Finally, conservation of momentum specifies that the gradient in total stress, P+p, must be zero:

$$\frac{\partial(P + p)}{\partial x} = 0 \quad (A10)$$

Transport of Permeating Solute

The intramembrane solute flux can also be written as the sum of diffusive, electrophoretic and electroosmotic components:

$$\Gamma_s = \phi\left(-\overline{D}_s \frac{\partial \overline{c}_s}{\partial x} + \overline{\mu}_s \overline{c}_s E\right) + W_s \overline{c}_s U \quad (A11)$$

and must satisfy the continuity condition $$\frac{\partial}{\partial t}(H\overline{c}_s) = -\frac{\partial(\alpha \Gamma_s)}{\partial \psi} \quad (A12)$$

$W_s$ is a hindrance factor for convective transport which depends on the solute size and hydrodynamic interactions. The intramembrane diffusivity $\overline{D}_s$ and electrophoretic mobility $\overline{\mu}_s$ will differ from their free solution values by similar, but not necessarily identical, hindrance factors. Both macroscopic statistical approaches (Yasuda, H., et al., *Makromolek Chem.* 126:177-186, (1969)) and pore models which take into account membrane microstructure (Deen, W. M., *AIChE J.* 33:1409-1425, (1987)) have been used to describe hindered transport.

Chemically Induced Flux Changes

Equations (A1)-(A5) and (A7)-(A10) constitute a general description of poroelastic swelling of the membrane coupled to or produced by changes in the electrolyte bath composition or applied fields. Limiting forms of this model are now applied to the specific experimental conditions of FIGS. 3-8. A striking feature of the transient hydration data of FIG. 3 is the relatively slow swelling time compared to the much faster deswelling time. This is consistent with the correspondingly slow (fast) changes in Lis-DEX flux following an increase (decrease) in bath pH. It was therefore tested whether the diffusion-reaction kinetics embodied in Equations (A1)–(A5) alone are sufficient to model the pH-induced changes in swelling (FIG. 3), or whether the mechanical dynamics of Equations (A7)–(A10) are also rate-limiting when coupled to Equations (A1)–(A5).

Since H$^+$ is a minority carrier in these experiments, the flux of H$^+$ is essentially uncoupled electrically from the fluxes of the other mobile ions, i.e.. K$^+$ and Cl$^-$. Helfferich, F., *Ion Exchange*, McGraw-Hill, (1962). Thus, in the absence of an applied electric field, the H$^+$ electrical migration term in Equation (A1) may be neglected. The convection term is also neglected due to the absence of a transmembrane pressure drop and the insignificant fluid velocity due to membrane swelling. The combination of Equations (A1), (A3) and (A4) results in a nonlinear, hydration dependent diffusion equation for $\bar{c}_H$:

$$\frac{\partial}{\partial t}\left[c_H\left(H + \frac{c^s_{mo}}{K + c_H}\right)\right] = \frac{\partial}{\partial \psi}\left(a\phi D_H \frac{\partial c_H}{\partial x}\right) \quad (A13)$$

For the case of uniaxial swelling, the normalized area $\alpha$ is unity and the transformation from the fixed coordinates to the material coordinates is given by $dx = (1+H)d\psi$. The mechanical rate processes embodied in Equations (A7)–(A10) are coupled to chemical diffusion-reaction in Equation (A13) via the hydration H. When changes in $c_H$ and H are very small, Equation (A13) may be linearized to give $$\frac{\partial c_H}{\partial t}\left[1 + \frac{Kc^s_{mo}/H_o}{(K + c_H^o)^2}\right] = D_H \frac{\partial^2 c_H}{\partial x^2} \quad (A14)$$

This diffusion-reaction equation describes perturbations in $c_H$ about an initial equilibrium $c^o_H$ and $H_o$ which have the characteristic time constant. Nussbaum, J. H. and Grodzinsky, A. J., *J. Membrane Sci.*, 8:193–219, (1981).

$$\tau_{dr} = \frac{\delta^2}{\pi^2 D_H}\left[1 + \frac{Kc^s_{mo}/H_o}{(K + c_H^o)^2}\right] \quad (A15)$$

The diffusion-reaction time $\tau_{dr}$ is much shorter at pH 3 where $\bar{c}_H >> K$, than at pH 6, where $\bar{c}_H \sim K$. This is qualitatively consistent with the observed asymmetry in time response between a change from pH 3 to 6 and a change from pH 6 to 3 (FIG. 3). The actual experiments of FIG. 3, however, involve large changes in pH; therefore, numerical solutions were used as described below.

Mechanical rate processes are described by combining Equations (A7)–(A10), which gives a mechanical diffusion equation in terms of elastic and hydraulic properties of the membrane:

$$\frac{\partial H}{\partial t} = \frac{\partial}{\partial \psi}\left[\alpha k \frac{\partial}{\partial x}\left(M\frac{H - H_{eq}}{1 + H_{eq}}\right)\right] \quad (A16)$$

The effective hydraulic permeability k was obtained by eliminating the electric field E from Darcy's law (Equation (A7)) using Equations (A1), (A2) and (A5). When there is no applied field (J=O) and E is due entirely to fluid flow relative to the solid membrane matrix (streaming potential):

$$k = \frac{k'\phi\Sigma\bar{\mu}_i|z_i|\bar{c}_i}{\phi\Sigma\bar{\mu}_i|z_i|c_i + k'(z_m\bar{c}_m)^2 F} \quad (A17)$$

When changes in H are small, the solution of Equation (A16) for free-swelling boundary conditions and no chemical gradients, is characterized by the gel swelling time constant. Tanaka, T. and Fillmore, D. J., *J. Chem. Phys.* 70:1214–1218, (1979).

$$\tau_{mech} = \frac{\delta^2}{\pi^2 Mk} \quad (A18)$$

where the product of the equilibrium bulk longitudinal modulus M and the hydraulic permeability k constitute a diffusivity for mechanical deformation in a poroelastic material. Tanaka, T. and Fillmore, D. J., *J. Chem. Phys.*, 70:1214–1218, (1979); Chandler, R. N. and Johnson, D. L., *J. Apply. Phys.*, 52:3391–3395, (1981).

The ratio $\tau_{dr}/\tau_{mech}$ is a measure of the relative rates of the coupled chemical and mechanical diffusion processes in our experiments. Previous studies have shown that the kinetics of pH-induced mechanical deformation in polyelectrolyte membranes are dominated by diffusion-reaction processes when $\tau_{dr}$ is much longer than $\tau_{mech}$, the time needed to achieve mechanical equilibrium. Nussbaum, J. H. and Grodzinsky, A. J., *J. Membrane Sci*, 8:193–219 (1981). Based on mechanical measurements on PMAA membranes (M$\neq$40 kPa at pH 3 and 75 kPA at pH 6 for S.05/1 membrane in 50 mM KCl), hydration data and the known chemical constants, it is estimated that this ratio could vary from as low as 0.05 at PH 3 to as high as 80 at pH 6. Thus, at low pH, the mechanical dynamics could retard the chemically induced changes in hydration, whereas at higher pH the chemical diffusion-reaction kinetics would be rate limiting.

To test this hypothesis the coupled Equations (A13) and (A16) were solved numerically using the Crank-Nicholson method. Crank, J., *The Mathematics of Diffusion*, Clarendon Press, Oxford (1975). This was compared with a solution of Equation (A13) alone assuming instantaneous mechanical equilibrium (i.e., H=H$_{eq}$ at each instant t and at each position x). The S.05/1 PMAA membrane hydration data in 50 mM solution (FIG. 2) was used in the constitutive law (A9) for H$_{eq}$ in terms of $\bar{c}_H$, which is calculated from the bath pH. The carboxyl group density for PMAA is $\bar{c}^s_{mo}$=15.4 mol per liter of solid polymer, and the dissociation constant was previously measured to be K=10$^{-5.5}$. Nussbaum, J. H., Ph.D. Thesis MIT EECS, (1986). The intramembrane diffusivity of H$^+$ was determined from the dilute solution diffusivity=(D$^\infty_H$9.3$\times$10$^{-9}$ m$^2$/s), (Weast, *CRC Handbook of Phys. and Chem.*, 55th Ed., P. D132, CRC Press, Ohio, (1975)), modified by a tortuosity factor derived for ion diffusion in ion exchange membranes (Mackie, J. S. and Meares, P., *Proc. R. Soc. A.* 232:498–509, (1955)):

$$\bar{D}_i = D_i^\infty\left(\frac{H}{(2 + H)}\right)^2 \quad (A19)$$

A mechanical diffusivity of $Mk=1.7\times10^{-11} m^2/s$ for the S.05/1 membrane was estimated from measurements of the modulus at pH 6 and the electroosmositic coefficient at pH 7. Boundary conditions on $\bar{c}_H$ at $\psi=0$ and $\psi=\delta_o/(1+H_o)$ were fixed by the pH of the external bath solutions, since the ions must satisfy the Donnan equilibrium (A6) and the electroneutrality condition (A5) at each membrane-bath interface. Free-swelling mechanical boundary conditions were maintained by setting $H=H_{eq}$ at $\psi=0$ and $\psi=\delta_o/(1+H_o)$ There were no adjustable parameters.

FIGS. 11-14 show the predicted hydration versus time for membranes cast to thicknesses of 125, 250, 500 and 1000 μm, respectively, compared to the data of FIG. 3. In each plot the solid curve corresponds to the case of instantaneous mechanical equilibrium (Equation A13) alone) and the dotted curve includes the mechanical kinetics (Equation (A13) plus Equation (A16)). The theory predicts slow hydration and rapid dehydration, which are consistent with the observed behavior. The assumption of an instantaneous mechanical equilibrium results in a more rapid initial swelling/deswelling but over a longer time scale the mechanical kinetics do not appear to be rate-limiting. Thus, FIGS. 11-14 suggest that mechanical rate processes (e.g., fluid flow and poroelastic behavior) are important during the initial transient. However, diffusionreaction kinetics play a dominant role in determining the transient behavior of pH-induced hydration changes and, by inference, the transient behavior of resulting changes in transmembrane solute flux (FIG. 4). Preliminary experiments indicate that similar pH-induced hydration changes are accelerated by the addition of a pH buffer to the membrane bathing solution in order to facilitate the transport of H+ ion-reaction process.

In FIGS. 11-14, the thinner membrane samples showed a slower increase in hydration than predicted by the theory; and the samples faster shrinking than predicted when the mechanical kinetics were included in the theory. The assumption of a constant Mk, made to simplify the solution of Equation (A16), may explain part of this discrepancy. There is evidence that both M and k increase as the membrane's charge and hydration increase Thus $\tau_{mech}$ would be slower when swelling from an initially collapsed state, and faster when shrinking from an initially swollen state. In addition, the model is derived here for uniaxial swelling; while this model does exhibit many of the observed trends, certain features inherent to the three-dimensional swelling of FIG. 3 may not be adequately represented by a one-dimensional model.

Electrically Induced Flux changes

In the electrical experiments of FIGS. 5-8, there were no ionic gradients across the membrane, allowing us to consider only that portion of the model relevant to electroosmosis and solute transport. Thus, in Equations (A3), (A4), (A8)-(A10), there are no spatial gradients in chemical or mechanical parameters.

Electroosmosis

With no fluid pressure drop across the membrane, Darcy's law (Equation (A7)) reduces to $$U = -k'z_m\bar{c}_m FE = k_iJ \quad (A20)$$

The right-hand equality defines the electroosmotic coupling coefficient. Helfferich, F., *Ion Exchange.*, McGraw-Hill, NY (1962):

$$k_i = \frac{-k'z_m\bar{c}_m}{\phi\Sigma\bar{\mu}_i|z_i|\bar{c}_i + k'(z_m\bar{c}_m)^2 F} \quad (A21)$$

which is obtained by using the ionic flux Equation (A1) and electroneutrality (A5) to express the fluid velocity in terms of the applied current density J. An average value of $k_i=3.2\times10^{-9} m^3/A$ s was obtained from direct measurements of the electroosmotic solvent flux across S.05/1 PMAA membranes in 0.1M CKl at pH 7. Based on this value the Darcy permeability is estimated from Equation (A21) to be $k'=2.7\times10^{-16} m^4/N$ s

Solute Transport

The solute flux Equation (A11) can be rewritten as $$\Gamma_s = -\phi\bar{D}_s\left(\frac{\partial \bar{c}_s}{\partial x} + \frac{Pe}{\delta_o}c_s\right) \quad (A22)$$

by introducing an effective Peclet number representing the ratio of electroosmotic convection plus electrophoretic transport to diffusive transport:

$$Pe = \delta_o\left(\frac{\phi\bar{\mu}_s E + W_s U}{\phi\bar{D}_s}\right) \quad (A23)$$

In the absence of electrophoresis, the magnitude of Pe is the familiar Peclet number. Insertion of this solute flux equation into the continuity Equation (A12) results in a diffusion equation for the permeating solute:

$$\frac{\partial \bar{c}_s}{\partial t} = \bar{D}_s\left(\frac{\partial^2 \bar{c}_s}{\partial x^2} + \frac{Pe}{\delta_o}\frac{\partial \bar{c}_s}{\partial x}\right) \quad (A24)$$

written here for the case of a uniformly hydrated membrane. The solution to Equation (A24) with $\partial \bar{c}_s/\partial t$ set to zero results in a steady-state transmembrane solute flux given by $$\Gamma_s' = \Gamma_s\frac{(d_o)}{(\phi c_s^M)} = \begin{cases} r_s\bar{D}_s & \text{for } Pe = 0 \\ r_s\bar{D}_s Pe(1 - e^{-Pe})^{-1} & \text{for } Pe \neq 0 \end{cases} \quad (A25)$$

where $c_s^M$ is the upstream solute concentration and $r_s$ where $r_s$ is an electrostatic partition coefficient.

From the pre field data of FIG. 6 (Table 2), the Peclet number was estimated using the independently measured electroosmotic coefficient $k_i$. (The electrophoretic mobility is zero here, since the solutes are neutral.) Taking $W_s$ in Equation (A23) to be unity, Equation (A25) was used to predict the steady-state flux of NSPA and Lis-DEX during application of a +100 A/m² and a −100 A/m² transmembrane current density. The value of $r_s\bar{D}_s$ was taken as the pre-field value of the normalized flux (Equation (A25)). The predicted Pe and steady-state flux for each solute are given in Table 3. For both solutes the measured flux enhancement for a positive current is greater than the prediction, and the measured flux suppression resulting from a negative current is less than the prediction. This discrepancy may be due, in part, to a spatially nonuniform current density in the experiments.

Transient Behaviour

The electrically induced flux changes observed in the PMAA and PA membranes (FIGS. 5-8) occurred much more rapidly than the pH-induced changes (FIG. 4). The low Reynold's number, fully developed flows that describe electrophoresis and electroosmosis are governed by charge relaxation and viscous diffusion times over molecular distances, which are essentially instantaneous on the time scale of interest. However, the adjustment of solute profiles, in response to an electrokinetic drive, is characterized by Equation (A24). The characteristic electrokinetic diffusion time associated with Equation (A24) is $$\tau_{ekd} = \frac{\delta^2}{\pi^2 \overline{D}_s} \left[ 1 + \left( \frac{Pe}{2\pi} \right)^2 \right]^{-1} \quad (26)$$

which is completely analogous to the electrodiffusion time for ionic species in charged membranes. Arndt, R. A. and Roper, C. D., *Simple Membrane Electrodiffusion Theory*, Physical Biological Sciences Misc., Blacksburg, Va. (1972). $\tau_{ekd}$ is on the order of 0.1-10 minutes for the membrane thicknesses of interest. Interaction between solute and membrane would further slow the response.

The magnitude and kinetics of changes in membrane hydration and permeability associated with electrodiffusion-control of intramembrane pH and ionic strength are now being quantified. Modelling of such phenomena requires solution of the coupled system of Equations (A1)-(A2).

TABLE 3

| | | Measured and Predicted Electrokinetic Solute Flux | | | | |
| | | Normalized flux: $\Gamma'_s(m^2/s)$ | | | | |
| | Calculated | Measured from Table 2 | | | Predicted by Eq(A25) | |
| Solute | [Pe] | Pre-field | +100 A/m² | −100 A/m² | +100 A/m² | −100 A/m² |
|---|---|---|---|---|---|---|
| NSPA | 0.16 | $3.8 \times 10^{-10}$ | $6.3 \times 10^{-10}$ | $3.7 \times 10^{-10}$ | $4.1 \times 10^{-10}$ | $3.5 \times 10^{-10}$ |
| Lis-DEX | 1.38 | $4.4 \times 10^{-11}$ | $1.4 \times 10^{-10}$ | $2.8 \times 10^{-11}$ | $8.1 \times 10^{-11}$ | $2.1 \times 10^{-11}$ |

Equivalents

Those skilled in the art will recognize, or be able to ascertain using no more than routine experimentation, many equivalents to the specific embodiment of the invention described specifically herein. Such equivalents are intended to be encompassed in the scope of the following claims.

We claim:

1. A method of dynamically controlled protein separation employing a polyelectrolyte membrane, wherein a selected protein is separated from a mixture of proteins, comprising:
   determining an appropriate pH and an appropriate ionic strength of an electrolyte bathing solution, and determining an electric field to be applied across the membrane;
   contacting each side of the membrane with the electrolyte bathing solution having a pre-selected pH and a pre-selected ionic strength, thereby producing the appropriate degree of membrane hydration to obtain a desired permeability of the polyelectrolyte member to each of the proteins in the mixture; and
   applying a pre-selected electric field across the membrane, thereby producing electroosmotic convention of each of the proteins in the mixture, within the membrane, such that the electroosmotic convention, either acting along or in combination with one or more effects selected from the group consisting of electromechanical deformation of the membrane matrix and effective pore size, changes in the electrostatic partitioning of each of the proteins in the mixture within the membrane, and electrophoresis of each of the proteins in the mixture within the membrane results in separation of the selected protein from the mixture of proteins across the polyelectrolyte membrane.

2. A method according to claim 1, wherein the selected protein is selected from the group consisting of albumin, interferon, insulin, ribonuclease A and interleukin-2.

3. A method of dynamically controlled protein separation employing a polyelectrolyte membrane, wherein a selected protein is separated from a mixture of proteins, comprising:
   determining an appropriate pH and an appropriate ionic strength of an electrolyte bathing solution and determining an electric field to be applied across a membrane;
   contacting both sides of the membrane with the electrolyte bathing solution having a pre-selected pH and a pre-selected ionic strength, thereby producing an ionic gradient across the membrane and producing the appropriate degree of membrane hydration to obtain a desired permeability of the polyelectrolyte membrane to each of the proteins in the mixture of proteins; and
   applying a pre-selected electric field across the membrane, thereby producing a net change in the ionization state of the polyelectrolyte membrane such that the resulting change in the electrostatic partitioning of each of the proteins in the mixture of proteins within the membrane, either acting alone or in combination with one or more effects selected from the group consisting of electromechanical deformation of the membrane matrix and effective pore size, electroosmotic convection of each of the proteins in the mixture of proteins within the membrane, and electrophoresis of each of the proteins in the mixture of proteins within the membrane results in separation of the selected protein from the mixture of proteins across the polyelectrolyte membrane.

4. A method according to claim 3, wherein the selected protein is selected from the group consisting of albumin, interferon, insulin, ribonuclease A and interleukin-2.

5. A method of dynamically controlled amino acid separation employing a polyelectrolyte membrane, wherein a selected amino acid is separated from a mixture of amino acids, comprising:

determining an appropriate pH and an appropriate ionic strength of an electrolyte bathing solution, and determining an electric field to be applied across the membrane;

contacting each side of the membrane with the electrolyte bathing solution having a pre-selected pH and a pre-selected ionic strength, thereby producing the appropriate degree of membrane hydration to obtain a desired permeability of the polyelectrolyte membrane to each of the amino acids in the mixture; and applying a pre-selected electric field across the membrane, thereby producing electroosmotic convection of each of the amino acids in the mixture, within the membrane, such that the electroosmotic convection, either acting alone or in combination with one or more effects selected from the group consisting of electromechanical deformation of the membrane matrix and effective pore size, changes in the electrostatic partitioning of each of the amino acids in the mixture within the membrane, and electrophoresis of each of the amino acids in the mixture within the membrane results in separation of the selected amino acid from the mixture of amino acids across the polyelectrolyte membrane.

6. A method of dynamically controlled amino acid separation employing a polyelectrolyte membrane, wherein a selected amino acid is separated from a mixture of amino acids, comprising:

determining an appropriate pH and an appropriate ionic strength of an electrolyte bathing solution, and determining an electric field to be applied across the membrane;

contacting each side of the membrane with the electrolyte bathing solution having a pre-selected pH and a pre-selected ionic strength, thereby producing an ionic gradient across the membrane and producing the appropriate degree of membrane hydration to obtain a desired permeability of the polyelectrolyte member to each of the proteins in the mixture of amino acids; and applying a pre-selected electric field across the membrane thereby producing a net change in the ionization state of the polyelectrolyte membrane such that the resulting change in the electrostatic partitioning of each of the amino acids in the mixture of amino acids within the membrane, either acting alone or in combination with one or more effects selected from the group consisting of electromechanical deformation of the membrane matrix and effective pore size, electroosmotic convection of each of the amino acids in the mixture of amino acids within the membrane, and electrophoresis of each of the amino acids in the mixtuer of amino acids within the membrane results in separation of the selected amino acid from the mixture of amino acids across the polyelectrolyte membrane.

7. A drug delivery system, which provides controlled delivery of a drug on demand, comprising:

a reservoir containing the drug, a polyelectrolyte membrane and an electrolyte bathing solution having a pre-selected pH and a pre-selected ionic strength; and a means for applying a pre-selected electric field across the membrane, thereby producing electroosmotic convention of the drug within the membrane, such that the electroosmotic convection, either acting alone or in combination with one or more effects selected from the group consisting of electromechanical deformation of the membrane matrix and effective pore size, changes in the electrostatic partitioning of the drug within the membrane and electrophoresis of the drug within the membrane results in selective transport of the drug across the polyelectrolyte membrane.

8. The drug delivery system of claim 7 further comprising a sensor means for providing real-time control of the delivery of the drug whereby the amount of drug delivered or time of drug delivery can be dynamically controlled.

9. A drug delivery system, which provides controlled delivery of a drug on demand, comprising:

a reservoir containing the drug, a polyelectrolyte membrane and an electrolyte bathing solution having a pre-selected pH and a pre-selected ionic strength; and a means for applying a pre-selected electric field across the membrane, thereby producing a net change in the ionization state of the polyelectrolyte membrane such that the resulting change in the electrostatic partitioning of the drug within the membrane, either acting along or in combination with one or more effects selected from the group consisting of electromechanical deformation of the membrane matrix and effective pore size, electroosmotic convection of the drug within the membrane, and electrophoresis of the drug within the membrane results in selective transport of the drug across the polyelectrolyte membrane.

10. The drug delivery system of claim 9 further comprising a sensor means for providing real-time control of the delivery of the drug whereby the amount of drug delivered or time of drug delivery can be dynamically controlled.

* * * * *

UNITED STATES PATENT AND TRADEMARK OFFICE
CERTIFICATE OF CORRECTION

PATENT NO. : 5,085,749

DATED : February 4, 1992

INVENTOR(S) : Paul E. Grimshaw, Alan J. Grodzinsky, Martin L. Yarmush

It is certified that error appears in the above-identified patent and that said Letters Patent is hereby corrected as shown below:

Claim 6, column 27, line 40, cancel "member" and insert therefor --membrane--;

Claim 6, column 27, line 40, cancel "proteins" and insert therefor --amino acids--;

Claim 6, column 28, line 1, cancel "mixtuer" and insert therefor --mixture--;

Claim 7, column 28, line 13, cancel "convention" and insert therefor --convection--.

Signed and Sealed this

Twenty-second Day of June, 1993

Attest:

MICHAEL K. KIRK

*Attesting Officer*   Acting Commissioner of Patents and Trademarks